(12) United States Patent
Lee

(10) Patent No.: US 12,090,347 B2
(45) Date of Patent: Sep. 17, 2024

(54) HIGH INTENSITY FOCUSED ULTRASONIC DEVICE WITH VERTICAL ASSEMBLY STRUCTURE

(71) Applicant: eCleo Co., Ltd., Seoul (KR)

(72) Inventor: Gayeon Lee, Gyeonggi-do (KR)

(73) Assignee: eCLEO Co., Ltd., Seoul (KR)

( * ) Notice: Subject to any disclaimer, the term of this patent is extended or adjusted under 35 U.S.C. 154(b) by 0 days.

(21) Appl. No.: 16/761,422

(22) PCT Filed: Mar. 5, 2020

(86) PCT No.: PCT/KR2020/095027
§ 371 (c)(1),
(2) Date: May 4, 2020

(87) PCT Pub. No.: WO2021/177579
PCT Pub. Date: Sep. 10, 2021

(65) Prior Publication Data
US 2022/0401760 A1    Dec. 22, 2022

(30) Foreign Application Priority Data
Mar. 4, 2020    (KR) .................. 10-2020-0027296

(51) Int. Cl.
*A61N 7/02*    (2006.01)
*A61N 7/00*    (2006.01)

(52) U.S. Cl.
CPC ........ *A61N 7/02* (2013.01); *A61N 2007/0034* (2013.01); *A61N 2007/0056* (2013.01)

(58) Field of Classification Search
CPC .............. A61N 7/02; A61N 2007/0034; A61N 2007/0056; A61N 2007/0082;
(Continued)

(56) References Cited

U.S. PATENT DOCUMENTS 10,639,006 B2    5/2020    Choi et al.
11,123,039 B2*   9/2021    Barthe .................. A61B 8/461
(Continued)

FOREIGN PATENT DOCUMENTS

JP    2013505789 A    2/2013
KR    101177691 B1    8/2012
(Continued)

OTHER PUBLICATIONS

Korea Intellectual Property Office, Office Action, Jun. 16, 2020.
(Continued)

*Primary Examiner* — Hien N Nguyen
(74) *Attorney, Agent, or Firm* — Umberg Zipser LLP

(57) ABSTRACT

According to an exemplary embodiment of the present disclosure, high intensity focused ultrasound device delivering high intensity focused ultrasound is disclosed. The high intensity focused ultrasound device comprising: a gripping part constituting a part of an outer housing of the high intensity focused ultrasound device and forming a grippable shape by a user, and an action part positioned at least partially on an extension line of a vertical cross-section of the gripping part and transmitting high intensity focused ultrasound generated from the high intensity focused ultrasound device to an outside.

17 Claims, 23 Drawing Sheets

(58) Field of Classification Search
CPC .... A61N 2007/0078; A61N 2007/0091; A61N 2007/025; A61B 34/25; A61B 2017/00026; A61B 2090/061; A61B 2090/064

See application file for complete search history.

(56) References Cited

U.S. PATENT DOCUMENTS

| | | |
|---|---|---|
| 2011/0072970 A1 | 3/2011 | Slobodzian et al. |
| 2011/0077556 A1 | 3/2011 | Bockenstedt et al. |
| 2014/0084949 A1 | 3/2014 | Smith et al. |
| 2018/0055478 A1 | 3/2018 | Choi et al. |

FOREIGN PATENT DOCUMENTS

| | | |
|---|---|---|
| KR | 101335476 B1 | 12/2013 |
| KR | 1020160019131 A | 2/2016 |
| KR | 1020160063119 A | 6/2016 |
| KR | 1020160075128 A | 6/2016 |
| KR | 20160080892 A | 7/2016 |
| KR | 1020160144755 A | 12/2016 |
| KR | 1020170065424 A | 6/2017 |
| KR | 101947688 B1 | 2/2019 |

OTHER PUBLICATIONS

European Patent Office, Rule 70(2) Communication, Feb. 20, 2024.
Japan Intellectual Property Office, Office Action dated Dec. 19, 2023; 4 pgs.

* cited by examiner

HIGH INTENSITY FOCUSED ULTRASONIC DEVICE WITH VERTICAL ASSEMBLY STRUCTURE

CROSS-REFERENCE TO RELATED APPLICATIONS

This application claims priority to and the benefit of Korean Patent Application No. 10-2020-0027296 filed in the Korean Intellectual Property Office on Mar. 4, 2020, the entire contents of which are incorporated herein by reference.

TECHNICAL FIELD

The present disclosure relates to a high intensity focused ultrasound device.

BACKGROUND ART

Recently, there have been technologies related to an ultrasound generating device that promotes treatment for the purpose of skin care and cure by using focused ultrasound generated by the ultrasound generating device.

Such an ultrasound generating device is mainly designed to have a hand piece and a cartridge which are separated from each other. In this case, the hand piece may be a body of the ultrasound generating device designed to make it easy for a user to grip the ultrasound generating device for use. Further, the cartridge may be a component which is embedded with an ultrasonic transducer for generating an ultrasound, and constituent elements required to operate the ultrasonic transducer, and coupled to the hand piece.

In the ultrasound generating device in the related art, the hand piece configured to be gripped by the user and the cartridge configured to generate the ultrasound are coupled to have a right-angled structure. The ultrasound generated by the above-mentioned structure is generated at a position spaced, at a predetermined distance in a horizontal direction, apart from a position at which the user grips the ultrasound generating device. For this reason, the user requires a large amount of force to bring the position of the ultrasound generating device, where the ultrasound is generated, into close contact with a patient. In addition, the position at which the ultrasound is generated cannot be accurately brought into close contact with the patient, which causes deterioration in efficiency.

Furthermore, the cartridge including the ultrasonic transducer is a consumable component that may generate the ultrasound only a predetermined number of times, and thus the cartridge needs to be frequently replaced if the efficiency deteriorates, which further causes a problem with costs.

Accordingly, there may be a need for a structure improved to smoothly transmit, to the patient, the ultrasound generated by the ultrasound generating device.

DOCUMENT OF RELATED ART

Patent Document

Korean Patent No. 10-1335476

SUMMARY OF THE INVENTION

The present disclosure has been made in an effort to provide a high intensity focused ultrasound device having a structure which is easy for a user to use.

Technical problems of the present disclosure are not limited to the aforementioned technical problems, and other technical problems, which are not mentioned above, may be clearly understood by those skilled in the art from the following descriptions.

The present disclosure has been made in an effort to provide a high intensity focused ultrasound device delivering high intensity focused ultrasound. An exemplary embodiment of the present disclosure provides a high intensity focused ultrasound device delivering high intensity focused ultrasound comprising: a gripping part constituting a part of an outer housing of the high intensity focused ultrasound device and forming a grippable shape by a user; and an action part positioned at least partially on an extension line of a vertical cross-section of the gripping part and transmitting high intensity focused ultrasound generated from the high intensity focused ultrasound device to an outside.

The high intensity focused ultrasound device, further comprising: a cartridge coupled detachably to a lower side of the outer housing in a vertical direction.

The action part is provided in a lower part of the cartridge.

A vertical center axis of the outer housing is located in a straight line with a vertical center axis of the cartridge.

The cartridge and the outer housing have a detachable coupling structure.

The coupling structure comprises a hook coupling structure, a fitting coupling structure, or a screw coupling structure.

The hook coupling structure is formed by at least one hook extending from the outer housing toward the cartridge and at least one hook groove provided in the cartridge to which the at least one hook is coupled.

The hook coupling structure is formed by at least one hook protruding from a region of the cartridge and at least one hook groove provided in the outer housing to which the at least one hook is coupled.

The fitting coupling structure is formed by an accommodation space recessed in the outer housing and a region of the cartridge inserted into the accommodation space.

A shape of the accommodation space corresponds to a shape of a region of the cartridge.

The screw coupling structure is formed by a rotational engagement of a screw thread existing in an accommodation space recessed in the outer housing and a screw thread existing in a region of the cartridge inserted into the accommodation space.

The outer housing comprises at least one coupling hole formed through a penetration to communicate with the accommodation space recessed in the outer housing, and wherein the cartridge, in case at least partially inserted in the accommodation space, comprises at least one coupling part which is formed to protrude outwards of the at least one coupling hole when being inserted into the at least one coupling hole.

A shape of the at least one coupling part corresponds to a shape of the at least one coupling hole.

According to the several exemplary embodiments of the present disclosure, it is possible to provide the high intensity focused ultrasound device having the structure which is easy for a user to use.

The effects obtained by the present disclosure are not limited to the aforementioned effects, and other effects, which are not mentioned above, will be clearly understood by those skilled in the art from the following description.

BRIEF DESCRIPTION OF THE DRAWINGS

Various aspects will be described with reference to the drawings, in which similar reference numerals are used to refer to similar components. In the following examples, for purposes of explanation, multiple specific details are set forth in order to provide a thorough understanding of one or more aspects. However, it will be apparent that such aspect(s) may be practiced without the specific details. In other examples, publicly known structures and devices are illustrated in block diagrams in order to easily describe one or more aspects.

DETAILED DESCRIPTION

Figure 1:
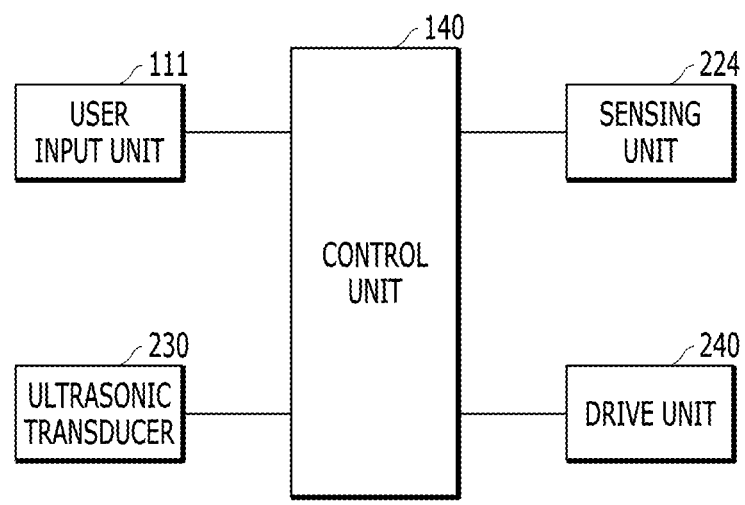
FIG. 1 is a block configuration view for explaining an example of a high intensity focused ultrasound device according to several exemplary embodiments of the present disclosure.

Various exemplary embodiments and/or various aspects will be disclosed with reference to the drawings. In the following descriptions, for explanation, multiple specific details are disclosed in order to provide overall understandings of one or more aspects. However, it will also be appreciated by those skilled in the art that this aspect(s) may be practiced without these specific details. The following descriptions and the accompanying drawings are provided for disclosing specific exemplary aspects of the one or more aspects in detail. However, these aspects are exemplary. Thus, some of the various methods in the principles of the various aspects may be used, and the descriptions are intended to include all such aspects and their equivalents. Specifically, "embodiment", "example", "aspect", "exemplary embodiment" and the like used in this specification may not be construed as any aspect or design described being better or more advantageous than other aspects or designs.

Hereinafter, the same or similar constituent elements are assigned with the same reference numerals regardless of reference numerals, and the repetitive description thereof will be omitted. In addition, in the description of the exemplary embodiment disclosed in the present specification, the specific descriptions of publicly known related technologies will be omitted when it is determined that the specific descriptions may obscure the subject matter of the exemplary embodiment disclosed in the present specification. In addition, the accompanying drawings are provided only to allow those skilled in the art to easily understand the exemplary embodiments disclosed in the present specification, and the technical spirit disclosed in the present specification is not limited by the accompanying drawings.

Terms "first", "second", and the like may be used to describe various elements and components, but the elements and components are of course not limited by these terms. These terms are merely used to distinguish one element or component from another element or component. Therefore, the first element or component mentioned hereinafter may of course be the second element or component within the technical spirit of the present disclosure.

Unless otherwise defined, all terms (including technical and scientific terms) used in the present specification may be used as the meaning which may be commonly understood by the person with ordinary skill in the art, to which the present disclosure belongs. In addition, terms defined in a generally used dictionary shall not be construed in ideal or excessively formal meanings unless they are clearly and specially defined in the present specification.

The term of "or" is intended to mean not an exclusive "or" but an inclusive "or". That is, unless specified or clear in context, "X uses A or B" is intended to mean one of the natural implicit substitutions. That is, "X uses A or B" can be applied to any of the cases where X uses A, X uses B, or X uses both A and B. Moreover, it is to be understood that the term "and/or" used in this specification refers to and includes all possible combinations of one or more of the listed related items.

It is to be understood that the terms "comprise (include)" and/or "comprising (including)" mean that the feature and/or a component is provided, but the presence or addition of one or more other features, other components and/or groups thereof are not excluded. In addition, unless specified or clear in the context of indicating a singular form, the singular in this specification and claims should generally be construed to mean "one or more".

When one constituent element is described as being "connected" or "coupled" to another constituent element, it should be understood that one constituent element can be connected or coupled directly to another constituent element, and an intervening constituent element can also be present between the constituent elements. When one constituent element is described as being "connected directly to" or "coupled directly to" another constituent element, it should be understood that no intervening constituent element is present between the constituent elements.

The suffixes "module" and "unit" used to describe some constituent elements in the following description are used together or interchangeably in order to facilitate the description in the specification, but the suffixes themselves do not have distinguishable meanings or functions.

When an element or layer is referred to as being "on" another element or layer, it can be directly on the other element or layer or intervening elements or layers may be present. In contrast, when an element is referred to as being "directly on" another element or layer, there are no intervening elements or layers present.

Spatially relative terms, such as "below," "beneath," "lower," "above," "upper," and the like, may be used herein for ease of description of one constituent element or a correlation between one constituent element and other constituent elements, as illustrated in the drawings. It should be understood that the spatially relative terms encompass different orientations of the elements in use or operation in addition to the orientation depicted in the drawings.

For example, if the constituent element in the drawings is turned over, the constituent element described as "below" or "beneath" the other constituent element may then be placed "above" the other constituent element. Thus, the exemplary term "below" can encompass both orientations of above and below. The constituent elements may be oriented in different directions, and the spatially relative terms used herein may be interpreted in accordance with the orientations.

Objects and effects of the present disclosure and technical constituent elements for achieving the objects and effects will be clear with reference to the exemplary embodiments described in detail below together with the accompanying drawings. In addition, in the description of the present disclosure, the specific descriptions of publicly known functions or configurations will be omitted when it is determined that the specific descriptions may unnecessarily obscure the subject matter of the present disclosure. In addition, the terms used herein are defined considering the functions in the present disclosure and may vary depending on the intention or usual practice of a user or an operator.

However, the present disclosure is not limited to the exemplary embodiments disclosed herein but will be implemented in various forms. The exemplary embodiments of the present disclosure are provided so that the present disclosure is completely disclosed, and a person with ordinary skill in the art can fully understand the scope of the present disclosure. The present disclosure will be defined only by the scope of the appended claims. Therefore, the definition of the present disclosure should be made based on the entire contents of the technology of the present specification.

In the present disclosure, a high intensity focused ultrasound device may create a skin cosmetic effect by generating ultrasound and changing positions at which the generated ultrasound is focused. However, the present disclosure is not limited thereto, and the high intensity focused ultrasound device according to the present disclosure may be used for various purposes.

According to several exemplary embodiments of the present disclosure, the high intensity focused ultrasound device may have an outer housing having a gripping part formed to enable a user to conveniently grip the high intensity focused ultrasound device, and a cartridge which is a consumable component that generates the ultrasound.

In this case, the cartridge may be coupled to a lower side of the outer housing so as to be detachable in a vertical direction. In addition, when the cartridge is coupled to the outer housing, a vertical center axis of the cartridge may be positioned on a straight line together with a vertical center axis of the outer housing. In this case, when the user holds the high intensity focused ultrasound device with one hand, the user may conveniently apply external force in a direction in which the ultrasound is generated. Hereinafter, the high intensity focused ultrasound device having a vertical structure according to the present disclosure will be described with reference to FIGS. 1 to 21.

FIG. 1 is a block configuration view for explaining an example of the high intensity focused ultrasound device according to the several exemplary embodiments of the present disclosure.

Referring to FIG. 1, a high intensity focused ultrasound device 10 may include a control unit 140, a user input unit 111, an ultrasonic transducer 230, a drive unit 240, and a sensing unit 224. However, the above-mentioned constituent elements are not essential to implement the high intensity focused ultrasound device 10. The high intensity focused ultrasound device 10 may have the constituent elements larger or smaller in number than the constituent elements listed above. In this case, each of the constituent elements may be configured as a separate chip, module, or device or may be included in a single device.

Typically, the control unit 140 may process an overall operation of the high intensity focused ultrasound device 10. The control unit 140 may provide the user with appropriate information or functions or process the information or functions by processing signals, data, information, and the like inputted or outputted through the user input unit 111 and by driving application programs stored in a storage unit (not illustrated). As an example, the control unit 140 may control the ultrasonic transducer 230 to generate the ultrasound based on an input from the user by means of the user input unit 111.

As another example, the control unit 140 may recognize, by means of the sensing unit 224, the contact between the high intensity focused ultrasound device 10 and at least a part of the user's body and then control the drive unit 240 to move the ultrasonic transducer 230. Hereinafter, a method of controlling, by the control unit 140, the operation of the ultrasonic transducer 230 will be described with reference to FIGS. 18 to 21, and the description of the ultrasonic transducer 230 and the drive unit 240 continues.

The user input unit 111 may be configured to receive, from the user, at least one mode for operating the ultrasonic transducer 230. When the mode is inputted through the user input unit 111, the control unit 140 may control the operation of the ultrasonic transducer 230 in accordance with the inputted mode. In this case, the mode may be related to a method of generating the ultrasound by the ultrasonic transducer 230. For example, when the control unit 140 recognizes that a first mode is inputted, the control unit 140 may control the ultrasonic transducer 230 to discontinuously generate the ultrasound at predetermined time intervals. However, the present disclosure is not limited thereto. Hereinafter, a mode for operating the ultrasonic transducer 230 will be described below with reference to FIGS. 18 to 21.

Meanwhile, the user input unit 111 may include mechanical input means (or, a mechanical key, for example, a button, a dome switch, a jog wheel, a jog switch, and the like). However, the present disclosure is not limited thereto.

Meanwhile, according to the present disclosure, the user input unit 111 may recognize the user's touch input by means of a touch sensor. In this case, the touch sensor may recognize the touch input based on at least one of a resistive type, a capacitive type, an ultrasonic type, or an electromagnetic type. However, the present disclosure is not limited thereto.

Meanwhile, according to the several exemplary embodiments of the present disclosure, when the touch input is recognized by the user input unit 111, the control unit 140 may control the high intensity focused ultrasound device 10 to generate the ultrasound in accordance with the first or second mode inputted by the user. Hereinafter, a mode for operating, by the control unit 140, the ultrasonic transducer 230 when the touch input is recognized by the user input unit 111 will be described below with reference to FIGS. 18 to 21.

Meanwhile, the ultrasonic transducer 230 may generate the ultrasound under control of the control unit 140. Further, the user's body may be irradiated with the ultrasound generated by the ultrasonic transducer 230.

The drive unit 240 may move the ultrasonic transducer 230 under control of the control unit 140.

Specifically, the ultrasonic transducer 230 and the drive unit 240 may be provided in the cartridge coupled to the lower side of the high intensity focused ultrasound device 10. Further, the drive unit 240 may move the ultrasonic transducer 230 in a horizontal direction in the cartridge under control of the control unit 140. However, the present disclosure is not limited thereto.

Meanwhile, in the present disclosure, the cartridge may be a component which is coupled to the high intensity focused ultrasound device 10, has therein the ultrasonic transducer 230 and the drive unit 240, and generates the ultrasound. The cartridge may be detachably coupled to the lower side of the high intensity focused ultrasound device 10. The maximum number of times the cartridge is used may be 10,000 shots. However, the present disclosure is not limited thereto.

Hereinafter, the cartridge will be described below in detail with reference to FIGS. 2 to 4.

The sensing unit 224 may include one or more sensors configured to sense at least one of information about the inside of the high intensity focused ultrasound device 10 and information about a peripheral environment around the high intensity focused ultrasound device 10.

For example, the sensing unit 224 may include at least one of a proximity sensor, a touch sensor, an infrared (IR) sensor, an ultrasonic sensor, a conductor sensor, and a temperature sensor. However, the present disclosure is not limited thereto.

Meanwhile, in the present disclosure, when the control unit 140 recognizes, by the sensing unit 224, that a region of the high intensity focused ultrasound device 10 is in contact with at least a part of the user's body, the control unit 140 may control the ultrasonic transducer 230 to generate the ultrasound. Hereinafter, a method of controlling, by the control unit 140, the ultrasonic transducer 230 by means of the sensing unit 224 will be described below with reference to FIGS. 16 and 17.

According to the above-mentioned configuration, the high intensity focused ultrasound device 10 may generate the ultrasound by means of the ultrasonic transducer 230. In addition, the high intensity focused ultrasound device 10 may move the ultrasonic transducer 230 in the cartridge by means of the drive unit 240.

Meanwhile, in the present disclosure, the high intensity focused ultrasound device 10 may be manufactured to have a structure erected vertically. Hereinafter, an external appearance of the high intensity focused ultrasound device 10 according to the present disclosure will be described with reference to FIG. 2.

Figure 2:
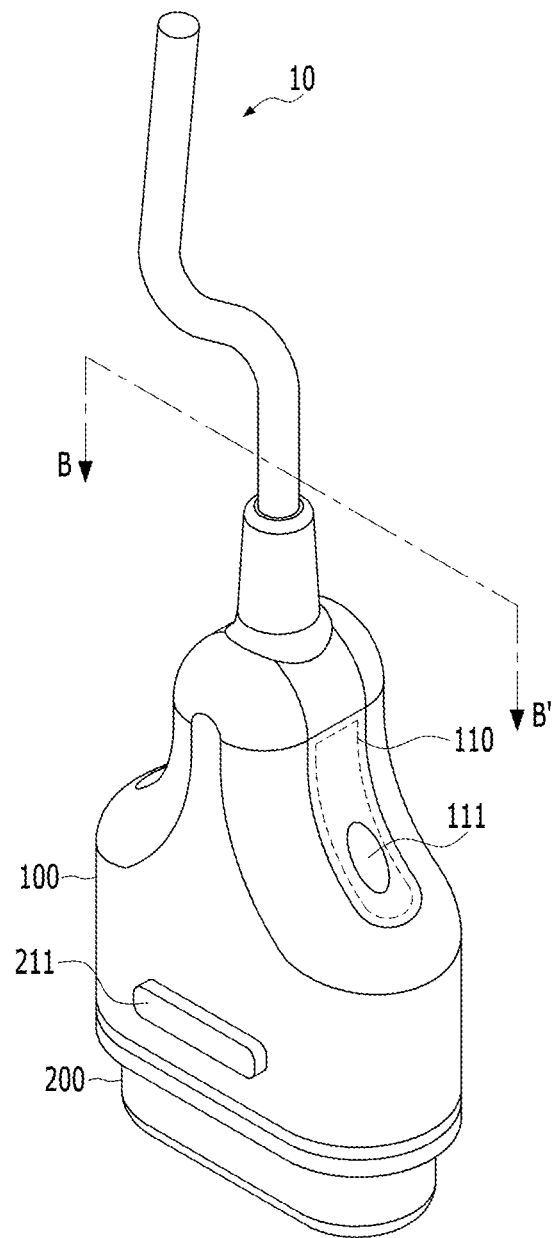
FIG. 2 is a perspective view for explaining an example of the high intensity focused ultrasound device according to the several exemplary embodiments of the present disclosure.

FIG. 2 is a perspective view for explaining an example of the high intensity focused ultrasound device according to the several exemplary embodiments of the present disclosure.

Referring to FIG. 2, the high intensity focused ultrasound device 10 may include an outer housing 100 and a cartridge 200. However, the above-mentioned constituent elements are not essential to implement the high intensity focused ultrasound device 10. The high intensity focused ultrasound device 10 may have the constituent elements larger or smaller in number than the constituent elements listed above.

The outer housing 100 may form a part of the external appearance of the high intensity focused ultrasound device 10.

Specifically, the outer housing 100 may form the external appearance in a region of the high intensity focused ultrasound device 10 which is gripped by the user. However, the present disclosure is not limited thereto.

Meanwhile, a power supply unit may be coupled to an upper part of the outer housing 100. The power supply unit may be supplied with external power by being controlled by the control unit 140 and may supply power required to operate the respective constituent elements. However, the present disclosure is not limited thereto.

In the present disclosure, the outer housing 100 may include a light output part (not illustrated). In this case, the control unit 140 may turn on a light emission diode (LED) included in the light output part, thereby informing the user of whether the high intensity focused ultrasound device 10 operates. However, the present disclosure is not limited thereto.

Meanwhile, the outer housing 100 may include a gripping part 110. In this case, the gripping part 110 may be a part of the outer housing 100 formed to allow the user to conveniently grip the high intensity focused ultrasound device 10. However, the present disclosure is not limited thereto.

Meanwhile, the gripping part 110 may further include the user input unit 111. Since the user input unit 111 is provided on the gripping part 110, the user may conveniently operate the high intensity focused ultrasound device 10 even while holding the high intensity focused ultrasound device 10 with one hand.

The cartridge 200 is detachably coupled to the lower side of the outer housing 100 in the vertical direction and may generate the ultrasound.

Specifically, the cartridge 200 may have therein the ultrasonic transducer 230 configured to generate the ultrasound. Further, the interior of the cartridge 200 may be filled with an ultrasonic transmission medium that transmits the ultrasound, generated by the ultrasonic transducer 230, to the outside. Therefore, the ultrasound generated by the ultrasonic transducer 230 may be transmitted to the outside through the ultrasonic transmission medium. However, the present disclosure is not limited thereto. Hereinafter, the constituent elements included in the interior of the cartridge 200 will be described below with reference to FIGS. 4 to 14.

Meanwhile, according to the several exemplary embodiments of the present disclosure, the cartridge 200 may include at least one coupling part 211 so as to be coupled to the outer housing 100. Further, the outer housing 100 may have at least one coupling hole to which at least one coupling part 211 is coupled. In this case, the cartridge 200 may be detachably coupled to the outer housing 100.

Meanwhile, according to the several exemplary embodiments of the present disclosure, the cartridge 200 and the outer housing 100 may have a detachable coupling structure.

For example, the coupling structure may include a hook coupling structure, a fitting coupling structure, or a screw coupling structure. However, the present disclosure is not limited thereto. Hereinafter, the coupling structure of the outer housing 100 and the cartridge 200 will be described below with reference to FIG. 3.

Meanwhile, according to several exemplary embodiments of the present disclosure, a vertical center axis of the cartridge 200 may be positioned on a straight line together with a vertical center axis of the outer housing 100. In this case, external force, which the user applies in the vertical direction while gripping the outer housing 100, may be fully transmitted toward the portion of the cartridge 200 which comes into contact with a patient's skin. However, the present disclosure is not limited thereto.

Meanwhile, according to the several exemplary embodiments of the present disclosure, the external appearance of the outer housing 100 including the gripping part 110 and the external appearance of the cartridge 200 may be formed to be vertically symmetrical. In this case, the cartridge 200 and the outer housing 100 may be coupled to each other so that the vertical center axes thereof are clearly coincident with each other. However, the present disclosure is not limited thereto.

According to several other exemplary embodiments of the present disclosure, the outer housing 100 may include the gripping part 110, and an accommodation space 120 for accommodating the cartridge 200 may be formed in the vertical direction of the internal space of the outer housing 100 which is formed by the gripping part 110. The cartridge 200 may include a first casing 210 formed to be engaged with an inner wall of the accommodation space 120. The cartridge 200 may have an action part 222 formed on an extension line of a vertical cross-section of the gripping part 110 and configured to transmit high intensity focused ultrasound to the outside.

The action part 222 may be entirely or at least partially included on the extension line of the vertical cross-section of the gripping part 110. Since a region of the action part 222, through which the high intensity focused ultrasound is transmitted to the outside, is at least partially or entirely included on the extension line of the vertical cross-section of the gripping part 110, the user of the high intensity focused ultrasound device 10 according to the present disclosure may intuitively recognize that the high intensity focused ultrasound is projected onto the patient's body on the extension line of the gripping part 110. This configuration may improve precision and operational characteristics when the user controls a portion onto which the high intensity focused ultrasound is projected.

The internal components of the cartridge 200 may be aligned so that the action part 222 is at least partially or entirely positioned on the extension line of the vertical cross-section of the gripping part 110 as described above. An exemplary embodiment of an aligned state of the internal components of the cartridge 200 will be described in detail with reference to FIGS. 4 to 9.

According to the above-mentioned configuration, the cartridge 200 of the high intensity focused ultrasound device 10 may be provided in the vertical direction at the lower side of the outer housing 100. Therefore, the user may grip the gripping part 110 of the outer housing 100 and easily bring the cartridge 200 into contact with the skin.

Meanwhile, according to the several exemplary embodiments of the present disclosure, the outer housing 100 and the cartridge 200 may include constituent elements, respectively, used to couple the outer housing 100 and the cartridge 200. Hereinafter, the coupling structure of the outer housing 100 and the cartridge 200 will be described with reference to FIG. 3.

Figure 3:
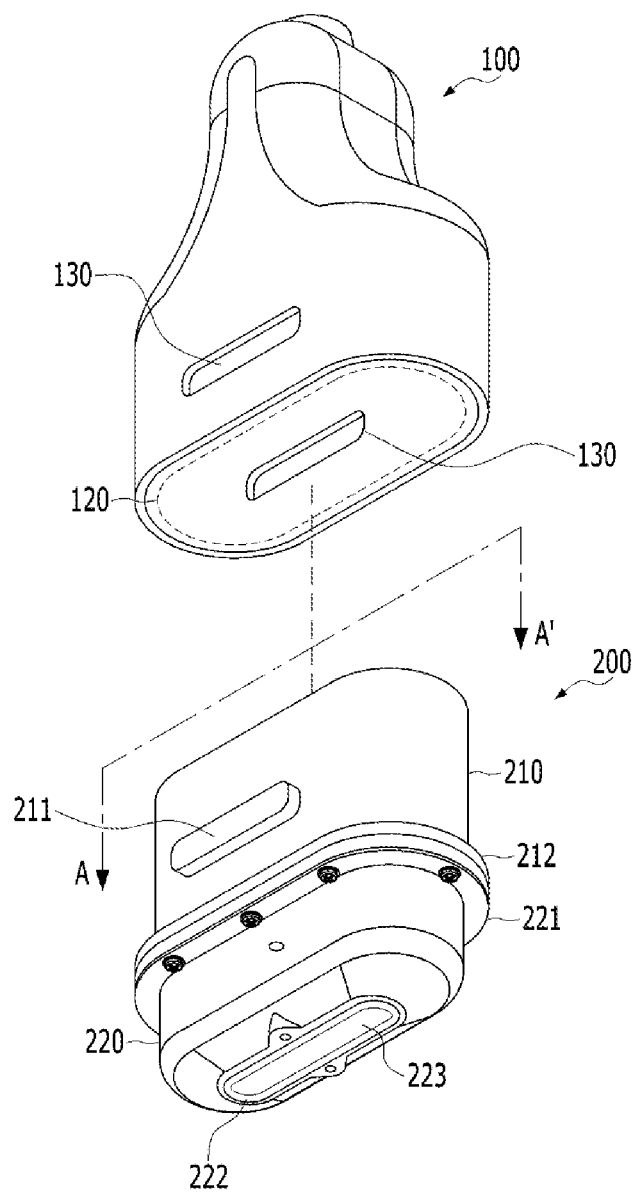
FIG. 3 is an exploded perspective view for explaining an example of the high intensity focused ultrasound device according to the several exemplary embodiments of the present disclosure.

FIG. 3 is an exploded perspective view for explaining an example of the high intensity focused ultrasound device according to the several exemplary embodiments of the present disclosure.

Referring to FIG. 3, the outer housing 100 may include the accommodation space 120 and at least one coupling hole 130. However, the present disclosure is not limited thereto.

The accommodation space 120 may be recessed at the lower end of the outer housing 100. Further, at least a part of the cartridge 200 may be inserted into the accommodation space 120.

Specifically, the accommodation space 120 may be recessed so that at least a part thereof has a shape corresponding to the first casing 210 for forming the external appearance at the upper side of the cartridge 200. Therefore, when the cartridge 200 and the outer housing 100 are coupled to each other, at least a part of the first casing 210 may be inserted into the accommodation space 120. However, the present disclosure is not limited thereto.

Meanwhile, in the present disclosure, the accommodation space 120 may be recessed so that the inside of the outer housing 100 is vertically symmetrical. Therefore, when at least a part of the cartridge 200 is inserted into the accommodation space 120, the vertical center axis of the outer housing 100 and the vertical center axis of the cartridge 200 may coincide with each other. However, the present disclosure is not limited thereto.

Meanwhile, at least one coupling hole 130 may be penetratively formed to communicate with the accommodation space 120. In this case, at least one coupling hole 130 may be a hole for fixing the cartridge 200.

Specifically, the cartridge 200 may have at least one coupling part 211 to be fixed to the outer housing 100. Further, when at least a part of the cartridge 200 is inserted into the accommodation space 120, at least one coupling part 211 may be inserted into at least one coupling hole 130. Therefore, the cartridge 200 may be fixed to the outer housing 100. However, the present disclosure is not limited thereto.

Meanwhile, according to the several exemplary embodiments of the present disclosure, the cartridge 200 and the outer housing 100 may be coupled to each other by a hook coupling structure, a fitting coupling structure, or a screw coupling structure. However, the present disclosure is not limited thereto, and the cartridge 200 and the outer housing 100 may be coupled by various coupling structures.

Figure 22A:
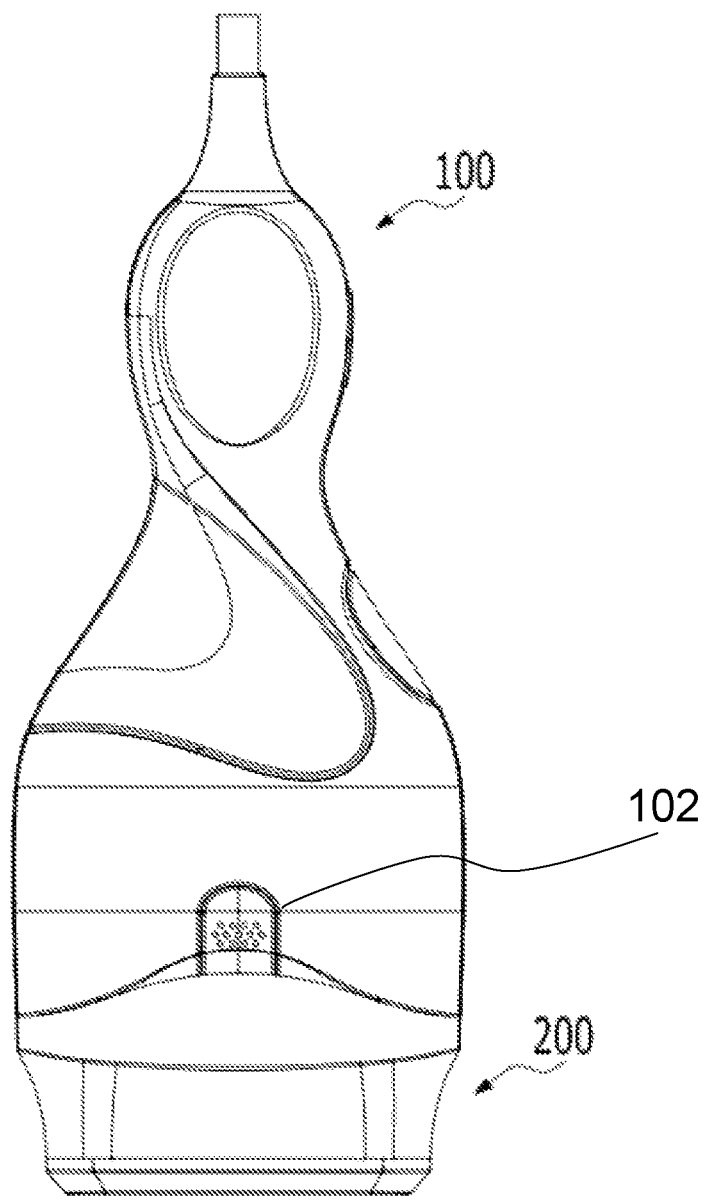
FIGS. 22A-22B are top and perspective views of an embodiment where the cartridge and the outer housing may be coupled to each other by a hook coupling structure.
Figure 22B:
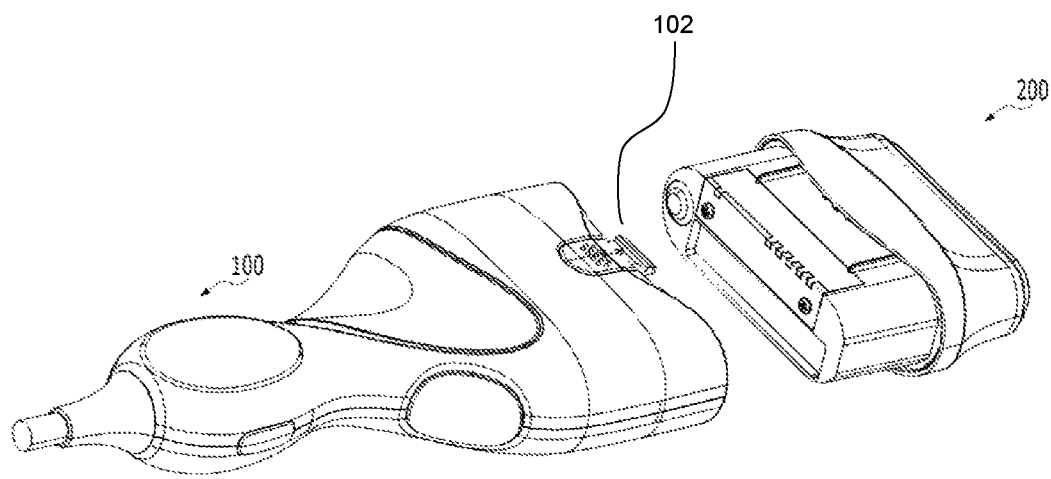

As an example shown in FIGS. 22A-22B, at least one hook 102 may be formed in the outer housing 100 and may extend toward the cartridge 200. Further, the cartridge 200 may have at least one hook groove to which at least one hook 102 is coupled. In this case, the outer housing 100 and the cartridge 200 may be coupled by the hook coupling structure.

As another example, the cartridge 200 may have at least one hook protruding from a region of the cartridge 200. In this case, the outer housing 100 may have at least one hook groove to which at least one hook is coupled. In this case, the outer housing 100 and the cartridge 200 may be coupled by the hook coupling structure.

As still another example, a shape of the accommodation space 120 may correspond to a shape of the region of the cartridge 200. In this case, the outer housing 100 and the cartridge 200 may be coupled by the fitting coupling structure formed by the accommodation space 120 recessed in the outer housing 100 and by the region of the cartridge 200 inserted into the accommodation space 120. In this case, the fitting may be a loose fit, an interference fit, a transition fit, and the like. However, the present disclosure is not limited thereto.

As yet another example, the accommodation space 120 recessed in the outer housing 100 may have a screw thread. Further, a screw thread may also be formed in the region of the cartridge 200 inserted into the accommodation space 120. In this case, the outer housing 100 and the cartridge 200 may be coupled by the screw coupling structure formed by the rotational engagement of the screw threads. However, the present disclosure is not limited thereto.

Meanwhile, a casing for forming the external appearance of the cartridge 200 may include the first casing 210 and a second casing 220.

That is, the cartridge 200 may be divided into the first casing 210 and the second casing 220. However, the present disclosure is not limited thereto, and the cartridge 200 may include two or more casings.

Meanwhile, according to the several exemplary embodiments of the present disclosure, the cartridge 200 may have a one-piece casing which is not divided into the first casing 210 and the second casing 220. However, the present disclosure is not limited thereto.

Meanwhile, the first casing 210 may include at least one coupling part 211 and a first catching part 212. However, the present disclosure is not limited thereto. At least one coupling part 211 may protrude outward from the region of the first casing 210. In this case, the region may be a region in which at least one coupling hole 130 is positioned when the first casing 210 is inserted into the accommodation space 120.

Specifically, when at least a part of the cartridge 200 is inserted into the accommodation space 120, at least one coupling part 211 may be inserted into at least one coupling hole 130 and may protrude outward from at least one coupling hole 130. Therefore, when at least a part of the cartridge 200 is inserted into the accommodation space 120, at least one coupling part 211 may couple the cartridge 200 to the outer housing 100. However, the present disclosure is not limited thereto.

Meanwhile, according to the several exemplary embodiments of the present disclosure, a shape of at least one coupling part 211 may correspond to a shape of at least one coupling hole 130. Therefore, at least one coupling part 211 may be inserted into at least one coupling hole 130 and may protrude outward from at least one coupling hole 130. However, the present disclosure is not limited thereto.

Meanwhile, in the present disclosure, when the cartridge 200 is coupled to the outer housing 100, the cartridge 200 and the outer housing 100 may be separated by the user's external force.

Specifically, when at least a part of the cartridge 200 is inserted into the accommodation space 120, at least one coupling part 211 may protrude outward from at least one coupling hole 130. Further, when the user applies external force to at least one coupling part 211 toward the inside of the cartridge 200, the cartridge 200 may be separated from the outer housing 100.

Meanwhile, according to the several exemplary embodiments of the present disclosure, the coupling part 211 may be made of a plastic-based or resin-based material. In this case, when external force is applied to at least one coupling part 211 toward the inside of the cartridge 200, the cartridge 200 may be deformed to be bent slightly inward. Therefore, the cartridge 200 and the outer housing 100 may be easily separated. However, the present disclosure is not limited thereto.

Meanwhile, the first catching part 212 may enable only at least a part of the cartridge 200 to be inserted into the accommodation space 120. Further, the first catching part 212 may be provided on the first casing 210.

Specifically, the first catching part 212 may be provided at a lower end of the first casing 210 and may protrude from an outer circumferential surface around the first casing 210. In this case, when the first casing 210 is inserted into the accommodation space 120, an upper surface of the first catching part 212 may be caught by a lower surface of the outer housing 100. Therefore, the first casing 210 may be inserted into the accommodation space 120 to a region in which the upper surface of the first catching part 212 is positioned. However, the present disclosure is not limited thereto.

Meanwhile, the second casing 220 may include a second catching part 221, the action part 222, and a window 223. However, the present disclosure is not limited thereto.

The second catching part 221 may be provided at an upper end of the second casing 220 and may protrude from an outer circumferential surface around the second casing 220. However, the present disclosure is not limited thereto.

Meanwhile, according to the several exemplary embodiments of the present disclosure, a region of the second catching part 221 may be in contact with the first catching part 212.

Specifically, when the first casing 210 and the second casing 220 are coupled, a lower surface of the first catching part 212 and an upper surface of the second catching part 221 may be in contact with each other. In this case, it is possible to prevent a leak of an ultrasonic transmission medium that fills an internal filling space formed by the first casing 210 and the second casing 220. However, the present disclosure is not limited thereto.

In this case, the ultrasonic transmission medium may mean a kind of transmission medium that smoothly transmits the ultrasound generated in the cartridge 200 to the outside. For example, the ultrasonic transmission medium may be a flowable solid or oil. In the related art, water may be used as the ultrasonic transmission medium. For this reason, in the case in which the drive unit 240 configured to move the ultrasonic transducer 230 is provided in the cartridge 200, the drive unit 240 may be corroded by water. In contrast, when oil is used as the ultrasonic transmission medium in the present disclosure, it is possible to prevent the drive unit 240 from being corroded even though the drive unit 240 is provided in the cartridge 200.

Meanwhile, according to the several exemplary embodiments of the present disclosure, at least one bolt is fastened to at least one fastening hole formed in each of the first catching part 212 and the second catching part 221, such that the first casing 210 and the second casing 220 may be coupled. Hereinafter, a method of coupling the first casing 210 and the second casing 220 will be described below with reference to FIGS. 14 to 15.

The action part 222 may be a region provided at the lower part of the cartridge 200 to transmit, to the outside, the high intensity focused ultrasound generated from the high intensity focused ultrasound device 10.

Specifically, the action part 222 may be at least partially positioned on the extension line of the vertical cross-section of the gripping part 110 of the outer housing 100.

More specifically, when the user grips, with one hand, the gripping part 110 of the high intensity focused ultrasound device 10 erected in the vertical direction, the user's fingers may be positioned in the horizontal direction. Further, the action part may be positioned in a direction orthogonal to the user's finger. Therefore, the user may conveniently bring the action part 222 into contact with a particular site of the body, on which the ultrasound is focused.

At a center of the action part 222 there may be provided an opening portion through which the high intensity focused ultrasound generated by the cartridge 200 passes to the outside. In this case, because the ultrasonic transmission medium or the like provided in the cartridge 200 may leak to the outside, the window 223 made of an ultrasonic transmitting material may be provided to block the opening portion. In addition, in the present disclosure, the window 223 may be an ultrasonic transmitting film made of polyimide or polymethyl pentene. However, the present disclosure is not limited thereto.

Meanwhile, the opening portion may be provided so that the external appearance of the lower surface of the second casing 220 is vertically symmetrical. However, the present disclosure is not limited thereto.

Meanwhile, according to the several exemplary embodiments of the present disclosure, the cartridge 200 may have a sealing member, for preventing a leak of the ultrasonic transmission medium, provided between the first catching part 212 and the second catching part 221. Hereinafter, the sealing member will be described below with reference to FIG. 13.

According to the above-mentioned configuration, the cartridge 200 may be coupled to the outer housing 100 so as to be easily detached in the vertical direction. In addition, the cartridge 200 may be attached and detached easily.

Meanwhile, in the present disclosure, the cartridge 200 may include several constituent elements for adjusting a position at which the ultrasound is generated and a position at which the generated ultrasound is focused. Hereinafter, the cartridge 200 according to the present disclosure will be described with reference to FIG. 4.

Figure 4:
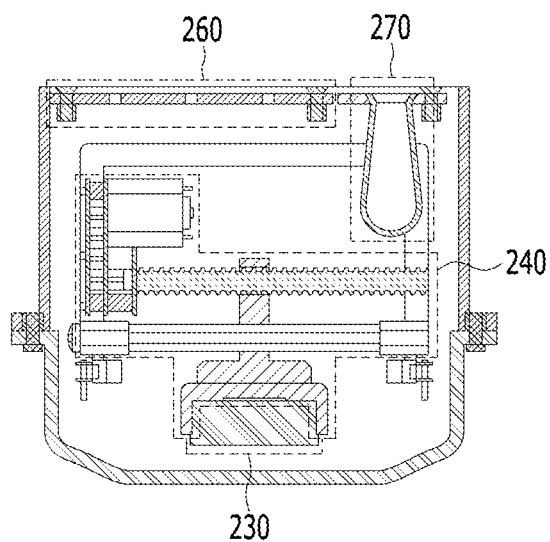
FIG. 4 is a cross-sectional view taken along line A-A' in FIG. 3 for explaining an example of a cartridge according to the several exemplary embodiments of the present disclosure.

FIG. 4 is a cross-sectional view taken along line A-A' in FIG. 3 for explaining an example of the cartridge according to the several exemplary embodiments of the present disclosure.

Referring to FIG. 4, the cartridge 200 may include the ultrasonic transducer 230, the drive unit 240, a cooling unit 260, and a buffer unit 270. However, the above-mentioned constituent elements are not essential to implement the cartridge 200. The cartridge 200 may have the constituent elements larger or smaller in number than the constituent elements listed above.

In the present disclosure, the ultrasonic transducer 230 may generate the ultrasound toward the lower side of the cartridge 200 under control of the control unit 140. Further, the ultrasound, which is generated toward the lower side, may be transmitted to the outside while penetrating the window 223. However, the present disclosure is not limited thereto.

The drive unit 240 is disposed in the cartridge 200 and may move the ultrasonic transducer 230 in the horizontal direction under control of the control unit 140.

Specifically, the drive unit 240 may include a drive motor configured to generate rotational force, at least one gear, and a moving module coupled to the ultrasonic transducer 230. Further, the drive unit 240 may move the ultrasonic transducer 230 horizontally by using the rotational force generated by the drive motor. Hereinafter, a method of moving, by the drive unit 240, the ultrasonic transducer 230 will be described below with reference to FIGS. 5 to 9.

Meanwhile, according to the several exemplary embodiments of the present disclosure, a range in which the drive unit 240 moves the ultrasonic transducer 230 horizontally may be equal to or smaller than a horizontal length of the opening portion. In this case, the ultrasound generated by the ultrasonic transducer 230 may be fully transmitted to the outside without being transmitted to the inside of the cartridge 200 even though the ultrasonic transducer 230 is moved horizontally by the drive unit 240. However, the present disclosure is not limited thereto.

Meanwhile, the cartridge 200 may be provided with the cooling unit 260. Further, the cooling unit 260 may remove heat of the ultrasonic transmission medium that fills the inside of the cartridge 200.

Specifically, the heat is generated by at least one of the operations of the drive unit 240 and the operation of generating the ultrasound by the ultrasonic transducer 230 such that a temperature of the ultrasonic transmission medium may be raised. In this case, if the ultrasonic transmission medium is not cooled, the first casing 210, the second casing 220, the drive unit 240, and the ultrasonic transducer 230, which form the external appearance of the cartridge 200, may be damaged. Therefore, the cartridge 200 may be provided with the cooling unit 260 in order to remove the heat generated in the ultrasonic transmission medium. However, the present disclosure is not limited thereto. Hereinafter, the cooling unit 260 will be described below with reference to FIGS. 10 to 11.

Meanwhile, at least a part of the buffer unit 270 is disposed in the cartridge 200, and the buffer unit 270 may maintain a constant pressure in the cartridge 200.

Specifically, when the ultrasonic transmission medium, which fills the inside of the cartridge 200, is heated, a volume of the ultrasonic transmission medium may be expanded. In this case, the buffer unit 270 may be shrunk to the extent that the volume of the ultrasonic transmission medium is expanded. Therefore, the buffer unit 270 may maintain a constant pressure in the cartridge 200. Hereinafter, the buffer unit 270 will be described below with reference to FIGS. 12 and 13.

Meanwhile, in the present disclosure, the drive unit 240 may be fixedly disposed in the cartridge 200. Further, the ultrasonic transducer 230 may be moved in the cartridge 200. Hereinafter, the drive unit 240 according to the present disclosure will be described with reference to FIG. 5.

Figure 5:
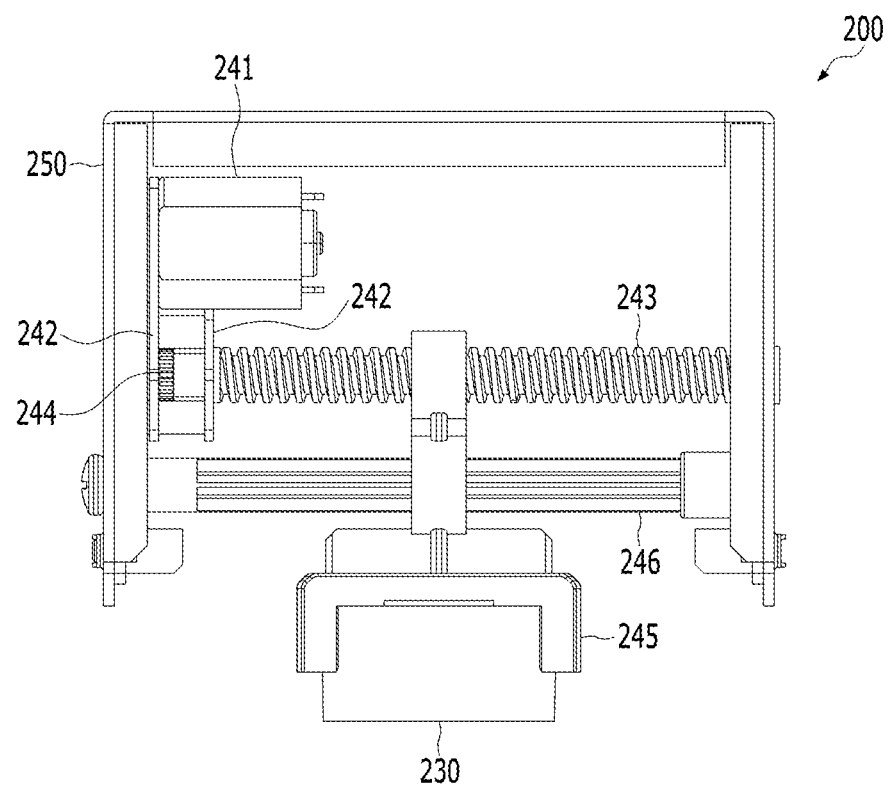
FIG. 5 is a view for explaining an example of a drive unit according to the several exemplary embodiments of the present disclosure.

FIG. 5 is a view for explaining an example of the drive unit according to the several exemplary embodiments of the present disclosure. In respect to the features in the contents illustrated in FIG. 5, overlapping with the features which have been described above with reference to FIGS. 1 to 4, the contents illustrated in FIGS. 1 to 4 will be referenced, and a detailed description thereof will be omitted.

Referring to FIG. 5, the cartridge 200 may include the ultrasonic transducer 230, the drive unit 240, and a bracket 250. However, the present disclosure is not limited thereto.

The bracket 250 may be fixedly coupled in the cartridge 200 and may fix the drive unit 240.

Specifically, the bracket 250 may have at least one of left and right supports and an upper end support for fixing the drive unit 240. Further, at least one of the left and right supports or the upper end support may be fixedly coupled to the cartridge 200.

For example, the bracket 250 may be fixed to an inner surface of the cartridge 200 by using a bolt, a screw, a rivet, a coupling pin, a bonding agent, or the like. However, the present disclosure is not limited thereto.

Meanwhile, a buffer unit hole, which is penetrated by at least a part of the buffer unit 270, may be provided in a region of the upper end support of the bracket 250. In this case, one end of the buffer unit 270 may be coupled to an upper end of the cartridge 200. However, the present disclosure is not limited thereto. Hereinafter, a shape of the buffer unit 270 will be described with reference to FIG. 12.

The drive unit 240 may include a drive motor 241, at least one support unit 242, a rotary unit 243, at least one gear 244, a moving module 245, and a guide unit 246. However, the above-mentioned constituent elements are not essential to implement the drive unit 240. The drive unit 240 may have the constituent elements larger or smaller in number than the constituent elements listed above.

The drive motor 241 may move the moving module 245 by transmitting rotational force to the rotary unit 243 through at least one gear 244.

For example, the drive motor 241 may move the moving module 245 to the right by rotating the rotary unit 243 clockwise.

As another example, the drive motor 241 may move the moving module 245 to the left by rotating the rotary unit 243 counterclockwise. However, the present disclosure is not limited thereto.

Meanwhile, the drive motor 241 may be an AC motor, a DC motor, a Brushless DC (BLDC) motor, or the like. However, the present disclosure is not limited thereto, and various motors may be used as the drive motor 241 according to the several exemplary embodiments of the present disclosure.

At least one support unit 242 may support the drive motor 241 and fix the drive unit 240 to the bracket 250.

For example, the drive motor 241 may be fixed to at least one support unit 242 by using a bolt, a screw, a rivet, a coupling pin, a bonding agent, or the like. However, the present disclosure is not limited thereto.

At least one gear 244 may transmit the rotational force, which is generated by the drive motor 241, to the rotary unit 243. In this case, the gears 244 may be combined to have different gear ratios, thereby partially reducing the rotational force generated by the drive motor 241. However, the present disclosure is not limited thereto. Hereinafter, a method of transmitting, by at least one gear 244, the rotational force to the rotary unit 243 will be described below with reference to FIG. 8.

Meanwhile, the rotary unit 243 may receive the rotational force generated by the drive motor 241.

Specifically, the rotary unit 243 may be rotatably coupled to at least one support unit 242. Further, the rotary unit 243 may receive the rotational force, which is generated by the drive motor 241, through at least one gear 244 rotatably coupled to at least one support unit 242. However, the present disclosure is not limited thereto.

Meanwhile, according to the several exemplary embodiments of the present disclosure, the rotary unit 243 may also receive the rotational force from the drive motor 241 through a pulley and a belt coupled to the pulley.

Specifically, a first pulley may be coupled to a shaft of the drive motor 241. Further, a second pulley may be coupled to one end of the rotary unit 243. In addition, the first pulley and the second pulley may be connected to each other through at least one belt. Therefore, the rotational force generated by the drive motor 241 may be transmitted to the rotary unit 243. However, the present disclosure is not limited thereto.

Meanwhile, in the present disclosure, a worm screw may be formed in a region of an outer circumferential surface of the rotary unit 243. That is, in the case in which the worm screw is formed in the region of the outer circumferential surface of the rotary unit 243, the moving module 245 may be moved in the horizontal direction by the rotation of the rotary unit 243. However, the present disclosure is not limited thereto.

Meanwhile, in the present disclosure, one end of the rotary unit 243 may be coupled to at least one gear 244, and the other end of the rotary unit 243 may be rotatably coupled to the bracket 250.

Specifically, the bracket 250 may have a hole on an imaginary line extending from a rotating shaft of the rotary unit 243. Further, a bearing or the like may be coupled to the hole provided in the bracket 250. Therefore, the other end of the rotary unit 243 may be rotatably coupled to the bracket 250. However, the present disclosure is not limited thereto.

Meanwhile, the moving module 245 is coupled to the rotary unit 243 and may be moved horizontally by the rotation of the rotary unit 243. Therefore, the moving module 245 may move the ultrasonic transducer 230 horizontally.

Specifically, the moving module 245 may include a fixing unit for fixing the ultrasonic transducer 230. In addition, the moving module 245 may include a bushing having an internal thread that meshes with the worm screw of the rotary unit 243, and the bushing is moved horizontally by the rotation of the rotary unit 243. Therefore, the moving module 245 may move the ultrasonic transducer 230 horizontally. Hereinafter, the moving module 245 will be described below with reference to FIG. 6.

The guide unit 246 may be fixed to the bracket 250 and may guide the horizontal movement of the moving module 245.

Specifically, an insertion hole into which the guide unit 246 is inserted may be provided in a region of the moving module 245. In this case, the region may be a region to which any shaft different from the rotating shaft of the rotary unit 243 may be coupled.

For example, the region may be a region between the bushing, which meshes with the rotary unit 243, and the fixing unit for fixing the ultrasonic transducer 230. However, the present disclosure is not limited thereto.

In this case, the guide unit 246 is coupled to the insertion hole and may prevent the moving module 245 from being rotated along with the rotation of the rotary unit 243. Therefore, the rotational force, which is transmitted to the moving module 245 through the rotary unit 243, may be converted into force for moving the moving module 245 in the horizontal direction. However, the present disclosure is not limited thereto. Meanwhile, the insertion hole provided in the moving module 245 will also be described below with reference to FIG. 6.

As described above, the guide unit 246 is coupled to the insertion hole H and may prevent the rotation of the moving module 245, but the present disclosure is not limited thereto. According to another exemplary embodiment of the present disclosure, the guide unit 246 may include any structure that aligns an operating end of the ultrasonic transducer 230 with one end of the cartridge 200.

As an example, a length of a fixing unit 2451 in a front-rear direction (a direction orthogonal to the horizontal direction in which the moving module 245 moves) may correspond to a length of the inner surface of the cartridge 200 in the front-rear direction. In this case, the fixing unit 2451 may be in contact with the inner surface of the cartridge 200 so that the operating end of the ultrasonic transducer 230 may be aligned with one end of the cartridge 200. In addition, since the fixing unit 2451 is in contact with the inner surface of the cartridge 200, the rotation of the moving module 245 may be prevented, and the moving module 245 may be moved in the horizontal direction by the rotation of the rotary unit 243. However, the present disclosure is not limited thereto.

Figure 6:
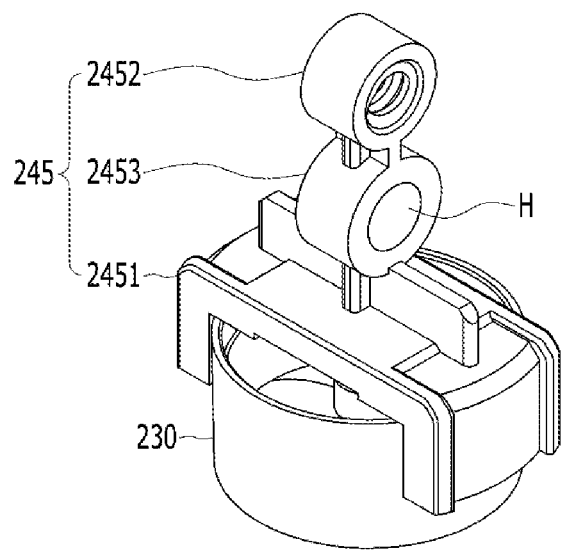
FIG. 6 is a perspective view for explaining an example of a moving module according to the several exemplary embodiments of the present disclosure.

FIG. 6 is a perspective view for explaining an example of the moving module according to the several exemplary embodiments of the present disclosure.

Referring to FIG. 6, the moving module 245 may include the fixing unit 2451, a bushing 2452, and a connecting part 2453. However, the present disclosure is not limited thereto.

The fixing unit 2451 may be provided at a lower side of the moving module 245 and may fix the ultrasonic transducer 230.

For example, the ultrasonic transducer 230 including a plurality of ultrasonic generating modules have a cylindrical external appearance. In this case, the fixing unit 2451 may be formed to surround at least a part of the external appearance of the ultrasonic transducer 230 and may fix the ultrasonic transducer 230. However, the present disclosure is not limited thereto.

The bushing 2452 may be provided at an upper side of the moving module 245. The bushing 2452 may have the internal thread that meshes with the worm screw provided on the rotary unit 243. Further, the bushing 2452 may receive the rotational force from the rotary unit 243.

In this case, if the rotation of the moving module 245 is not inhibited, the moving module 245 may be rotated by the rotational force transmitted through the bushing 2452. Therefore, in order to prevent the rotation of the moving module 245, the moving module 245 may include the connecting part 2453 provided between the fixing unit 2451 and the bushing 2452, and the guide unit 246 may be inserted into the connecting part 2453.

The connecting part 2453 may be provided between the fixing unit 2451 and the bushing 2452 and may connect the fixing unit 2451 and the bushing 2452. In addition, the connecting part 2453 may have the insertion hole H into which the guide unit 246 is inserted so that the moving module 245 slides along the guide unit 246. However, the present disclosure is not limited thereto.

According to the above-mentioned configuration, the moving module 245 may be coupled to the rotary unit 243 and the guide unit 246. Therefore, the moving module 245 may be moved in the horizontal direction by the rotation of the rotary unit 243.

Meanwhile, according to the several exemplary embodiments of the present disclosure, the drive motor 241 may be fixed to the bracket 250 by at least one support unit 242. In addition, at least one gear 244 may be rotatably coupled to at least one support unit 242. In this case, the drive motor 241 may transmit the rotational force to the rotary unit 243 through at least one gear 244. Hereinafter, a method of transmitting, by the drive motor 241 according to the present disclosure, the rotational force to the rotary unit 243 will be described with reference to FIGS. 7 and 8.

Figure 7:
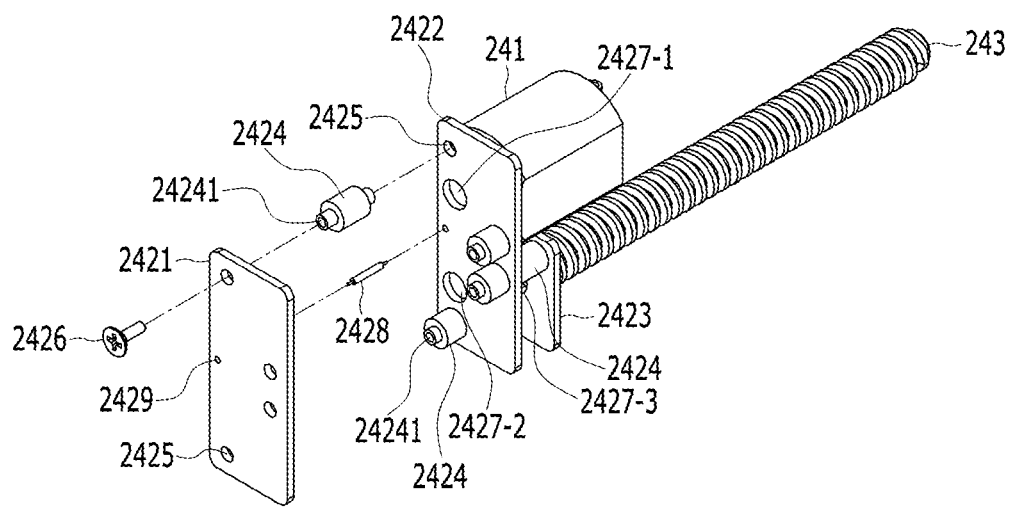
FIG. 7 is a view for explaining an example of a coupling relationship of at least one support unit according to the several exemplary embodiments of the present disclosure.

FIG. 7 is a view for explaining an example of a coupling relationship of at least one support unit according to the several exemplary embodiments of the present disclosure.

Referring to FIG. 7, at least one support unit 242 may include a first support unit 2421, a second support unit 2422, a third support unit 2423, at least one connecting rod 2424, and at least one first hole 2425. However, the present disclosure is not limited thereto.

The first support unit 2421 may be fixedly coupled to the bracket 250.

For example, the first support unit 2421 may be fixed to the bracket 250 by using a bolt, a screw, a rivet, a coupling pin, a bonding agent, or the like. However, the present disclosure is not limited thereto.

The second support unit 2422 may be provided to be spaced apart from the first support unit 2421.

Specifically, each of the first support unit 2421 and the second support unit 2422 may have at least one first hole 2425 at positions corresponding to each other. Further, the first support unit 2421 and the second support unit 2422 may be coupled to be spaced apart from each other by at least one connecting rod 2424 coupled to at least one first hole 2425.

More specifically, an outer diameter of each of both ends of at least one connecting rod 2424 may be coincident with an inner diameter of at least one first hole 2425. Further, one end of at least one connecting rod 2424 may be fitted with at least one first hole 2425 provided in the first support unit 2421, and the other end of at least one connecting rod 2424 may be fitted with at least one first hole 2425 provided in the second support unit 2422. In this case, an outer diameter of a region of at least one connecting rod 2424, except for both ends of at least one connecting rod 2424, may be larger than the inner diameter of at least one first hole 2425. Therefore, the first connecting member 2421 and the second connecting member 2422 may be coupled to be spaced apart from each other by at least one connecting rod 2424. However, the present disclosure is not limited thereto.

Meanwhile, at least one connecting rod 2424 may have a second hole 24241. In this case, the drive motor 241 may be coupled by the second hole 24241 and at least one bolt 2426.

Specifically, the drive motor 241 may have at least one bolt groove (not illustrated) provided in a region of a surface being in contact with the second support unit 2422, and at least one bolt 2426 may be fastened to the bolt groove. In this case, the region may be a region corresponding to a position at which at least one first hole 2425 is provided. In this case, at least one bolt 2426 may be fastened to at least one bolt groove while penetrating at least one first hole 2425 provided in the first support unit 2421, the second hole 24241, and at least one first hole 2425 provided in the second support unit 2422. Therefore, the drive motor 241 may be fixed to the second support unit 2422. However, the present disclosure is not limited thereto.

Meanwhile, the third support unit 2423 may be provided to be spaced apart from the second support unit 2422.

Specifically, each of the third support unit 2423 and the second support unit 2422 may have at least one first hole 2425 at the positions corresponding to each other. Further, the first support unit 2421 and the second support unit 2422 may be coupled to be spaced apart from each other by at least one connecting rod 2424 coupled to at least one first hole 2425. However, the present disclosure is not limited thereto.

Meanwhile, in the present disclosure, each of the second support unit 2422 and the third support unit 2423 may have at least one third hole 2427. In this case, at least one third hole 2427 may be a hole penetrated by at least one gear 244 seated between the support units 242.

For example, one surface of the drive motor 241, where a shaft (not illustrated) is provided, may be coupled to be in contact with one surface of the second support unit 2422. In this case, if no third hole 2427 is provided, the drive motor 241 cannot be coupled to the second support unit 2422 because of the shaft and at least one gear 244 fastened to the shaft. Therefore, at least one support unit 242 may have at least one third hole 2427 penetrated by the shaft or at least one gear 244. However, the present disclosure is not limited thereto.

Meanwhile, in the present disclosure, at least one coupling pin 2428 may be provided between the support units 242. In this case, at least one coupling pin 2428 may couple at least one gear 244 so that at least one gear 244 is rotatable between the support units 242.

Specifically, each of the first support unit 2421 and the second support unit 2422 may have at least one fourth hole 2429 in regions corresponding to each other. Further, at least one coupling pin 2428 may be rotatably coupled to at least one fourth hole 2429.

For example, an outer diameter of each of both ends of at least one coupling pin 2428 may be smaller than an inner diameter of at least one third hole 2429. Further, one end of at least one coupling pin 2428 may be rotatably coupled to at least one third hole 2429 provided in the first support unit 2429, and the other end of at least one coupling pin 2428 may be rotatably coupled to at least one third hole 2429 provided in the second support unit 2422. In this case, an outer diameter of a region of at least one coupling pin 2428, except for both ends of at least one coupling pin 2428, may be larger than the inner diameter of at least one third hole 2429. Therefore, at least one coupling pin 2428 may be provided between the first support unit 2421 and the second support unit 2422. However, the present disclosure is not limited thereto.

Meanwhile, at least one gear 244 may be fixedly coupled to at least one coupling pin 2428. Further, at least one coupling pin 2428 may be rotated along with the rotation of at least one gear 244.

Meanwhile, according to the several exemplary embodiments of the present disclosure, at least one gear 244 may transmit the rotational force, which is generated by the drive motor 241, to the rotary unit 243. Hereinafter, at least one gear 244 according to the present disclosure will be described with reference to FIG. 8.

Figure 8:
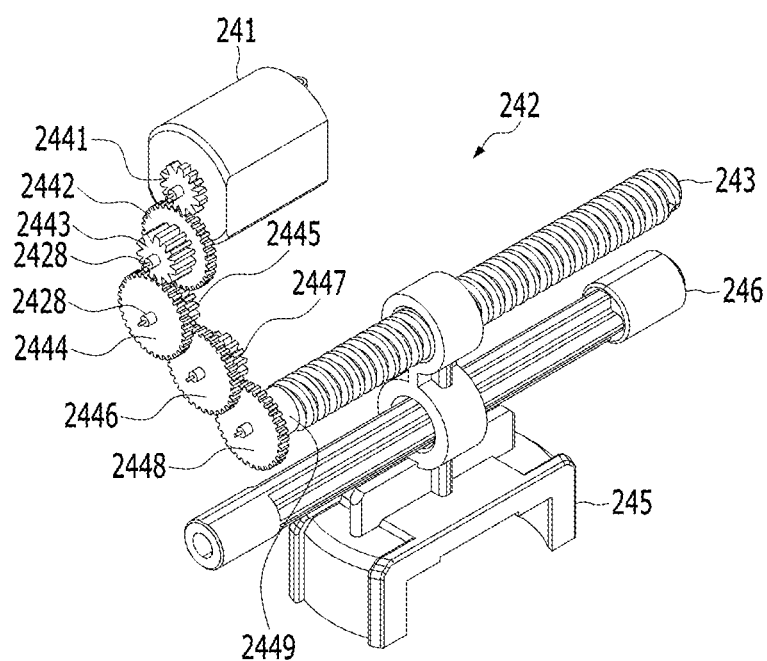
FIG. 8 is a view for explaining an example of at least one gear according to the several exemplary embodiments of the present disclosure.

FIG. 8 is a view for explaining an example of at least one gear according to the several exemplary embodiments of the present disclosure.

Referring to FIG. 8, the drive unit 240 may include the drive motor 241, a first gear 2441, a second gear 2442, a first cooperative gear 2443, a third gear 2444, a second cooperative gear 2445, a fourth gear 2446, a third cooperative gear 2447, a fifth gear 2448, and a connecting shaft 2449. However, the present disclosure is not limited thereto.

The first gear 2441 is coupled to the shaft (not illustrated) of the drive motor 241 and may receive the rotational force. In this case, the first gear 2441 may be provided to penetrate a third hole 2427-1 provided in the second support unit 2422. However, the present disclosure is not limited thereto.

The second gear 2442 meshes with the first gear 2441 and may receive the rotational force from the first gear 2441. In addition, the first cooperative gear 2443 is coupled to the second gear 2442 and may be rotated along with the rotation of the second gear 2442.

Specifically, the first cooperative gear 2443 may be coupled to one surface of the second gear 2442 so that a central axis of the first cooperative gear 2443 is coincident with a central axis of the second gear 2442. Further, the first cooperative gear 2443 and the second gear 2442 may be coupled to at least one coupling pin 2428 and provided between the first support unit 2421 and the second support unit 2422. However, the present disclosure is not limited thereto.

The third gear 2444 meshes with the first cooperative gear 2443 and may receive the rotational force from the first cooperative gear 2443. In addition, the second cooperative gear 2445 is coupled to the third gear 2444 and may be rotated along with the rotation of the third gear 2444.

Specifically, the first cooperative gear 2443 may be coupled to one surface of the second gear 2442 so that a central axis of the first cooperative gear 2443 is coincident with a central axis of the second gear 2442. Further, the first cooperative gear 2443 and the second gear 2442 may be coupled to at least one coupling pin 2428 and provided between the first support unit 2421 and the second support unit 2422. However, the present disclosure is not limited thereto.

The fourth gear 2446 meshed with the second cooperative gear 2445 and may receive the rotational force from the second cooperative gear 2445. In addition, the third cooperative gear 2447 is coupled to the fourth gear 2446 and may be rotated along with the rotation of the fourth gear 2446.

Specifically, the third cooperative gear 2447 may be coupled to one surface of the fourth gear 2446 so that a central axis of the third cooperative gear 2447 is coincident with a central axis of the fourth gear 2446.

Meanwhile, the third cooperative gear 2447 may be provided so that at least a part of the third cooperative gear 2447 penetrates a third hole 2427-2 provided in the second support unit 2422. In this case, a diameter of the third hole 2427-2 may be larger than an outer diameter of the third cooperative gear 2447. Therefore, at least a part of the third cooperative gear 2447 penetrates a third hole 2447-2, and the third cooperative gear 2447 may be rotatably provided. However, the present disclosure is not limited thereto.

Meanwhile, the fourth gear 2446 may be provided between the first support unit 2421 and the second support unit 2422 without penetrating the third hole 2447-2. However, the present disclosure is not limited thereto.

Meanwhile, the fifth gear 2448 meshes with the third cooperative gear 2447 and may receive the rotational force from the third cooperative gear 2447. In addition, the connecting shaft 2449 is coupled to the fifth gear 2448 and may be rotated along with the rotation of the fifth gear 2448. In this case, the connecting shaft 2449 may be a member for transmitting the rotational force from the fifth gear 2448 to the rotary unit 243. However, the present disclosure is not limited thereto.

Meanwhile, the connecting shaft 2449 may be provided so that at least a part of the connecting shaft 2449 penetrates a third hole 2427-3 provided in the third support unit 2423.

Specifically, one end of the connecting shaft 2449 may be coupled to one surface of the fifth gear 2448, and the other end of the connecting shaft 2449 may be coupled to the rotary unit 243 while penetrating the third hole 2427-3. Therefore, the fifth gear 2448 may transmit, to the rotary unit 243, the rotational force transmitted from the third cooperative gear 2447. However, the present disclosure is not limited thereto.

According to the above-mentioned configuration, the rotational force generated by the drive motor 241 may be transmitted to the rotary unit 243 through at least one gear 244. In addition, with the combination of at least one gear 244, the drive unit 240 may appropriately decelerate or accelerate the rotational speed of the rotary unit 243. However, the present disclosure is not limited thereto.

Meanwhile, according to the several exemplary embodiments of the present disclosure, the moving module 245 may be moved in the horizontal direction by the rotational force transmitted to the rotary unit 243. Hereinafter, an example in which the moving module 245 according to the present disclosure moves will be described with reference to FIG. 9.

Figure 9:
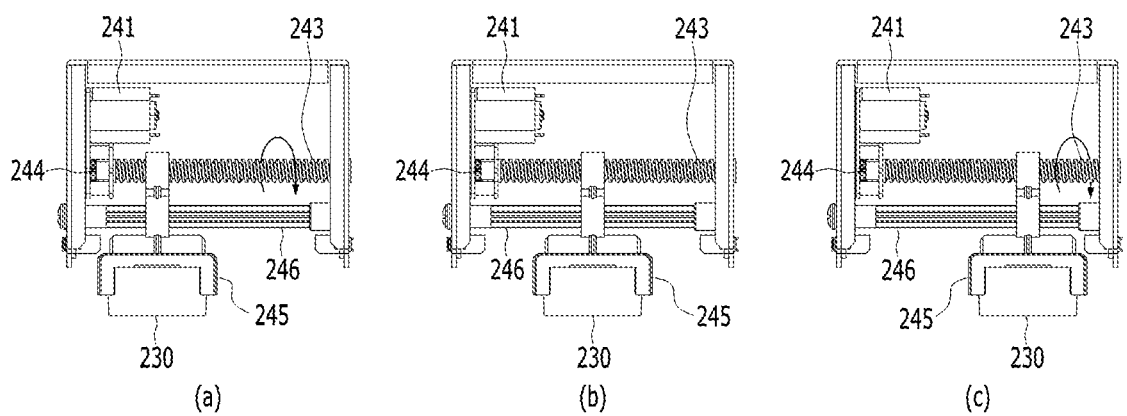
FIG. 9 is a view for explaining an example of a method of moving the moving module according to the several exemplary embodiments of the present disclosure.

FIG. 9 is a view for explaining an example of a method of moving the moving module according to the several exemplary embodiments of the present disclosure. FIG. 9A is a view for explaining an example in which the moving module according to the several exemplary embodiments of the present disclosure is moved to the left. FIG. 9B is a view for explaining an example in which the moving module according to the several exemplary embodiments of the present disclosure is positioned at a center. FIG. 9C is a view for explaining an example in which the moving module according to the several exemplary embodiments of the present disclosure is moved to the right.

First, referring to FIG. 9B, the moving module 245 according to the several exemplary embodiments of the present disclosure may be positioned at a center of the drive unit 240. In this case, the center of the drive unit 240 may be coincident with a center of the cartridge 200.

In this case, the ultrasound generated by the ultrasonic transducer 230 may be transmitted to the outside while penetrating the center of the window 223. That is, when the moving module 245 is positioned at the center of the drive unit 240, the ultrasound generated by the ultrasonic transducer 230 may be focused on a position extending from the vertical center axes of the outer housing 100 and the cartridge 200. Therefore, even though a position at which the ultrasound is generated cannot be visually recognized, a position on which the ultrasound is focused may be easily predicted. For example, without performing an additional operation, the user may recognize that the ultrasound, which is generated by the ultrasonic transducer 230, will be generated at the center of the high intensity focused ultrasound device 100. However, the present disclosure is not limited thereto.

Meanwhile, according to several other exemplary embodiments of the present disclosure, when the user makes an input, through the input unit 111 to turn off the power of the high intensity focused ultrasound device 10, the control unit 140 may control the drive unit 240 so that the moving module 245 is positioned at the center of the drive unit 240. Further, the control unit 140 may turn off the power of the high intensity focused ultrasound device 10. However, the present disclosure is not limited thereto.

Meanwhile, referring to FIG. 9A, the moving module 245 may be horizontally moved to the left as the rotary unit 243 rotates counterclockwise. In addition, referring to FIG. 9C, the moving module 245 may be horizontally moved to the right as the rotary unit 243 rotates clockwise. However, the present disclosure is not limited thereto, the moving module 245 may be horizontally moved to the right as the rotary unit 243 rotates clockwise, and the moving module 245 may be horizontally moved to the left as the rotary unit 243 rotates counterclockwise.

Meanwhile, according to the several exemplary embodiments of the present disclosure, a distance by which the moving module 245 may be moved to the left and a distance by which the moving module 245 may be moved to the right may be equal to each other. That is, the moving module 245 may be moved to be vertically symmetrical based on a vertical axis of the cartridge 200.

Meanwhile, according to the several exemplary embodiments of the present disclosure, the control unit 140 may control the ultrasonic transducer 230 so that the ultrasound is continuously generated for a predetermined period of time while the moving module 245 moves to the left and the right. Hereinafter, an operation of controlling, by the control unit 140, the ultrasonic transducer 230 while the moving module 245 moves will be described below with reference to FIGS. 18 to 21.

According to the above-mentioned configuration, the moving module 245 may be moved in the horizontal direction in the cartridge 200. In addition, the control unit 140 may control the ultrasonic transducer 230 so that the ultrasound is generated while the moving module 245 moves in the horizontal direction.

Meanwhile, according to the several exemplary embodiments of the present disclosure, the heat may be generated in the ultrasonic transmission medium, which fills the cartridge 200, as the drive unit 240 moves the moving module 245 to the left and the right or as the ultrasonic transducer 230 generates the ultrasound. In this case, the cartridge 200 may be provided with the cooling unit 260 for removing the generated heat. Hereinafter, the cooling unit 260 according to the present disclosure will be described with reference to FIG. 10.

Figure 10:
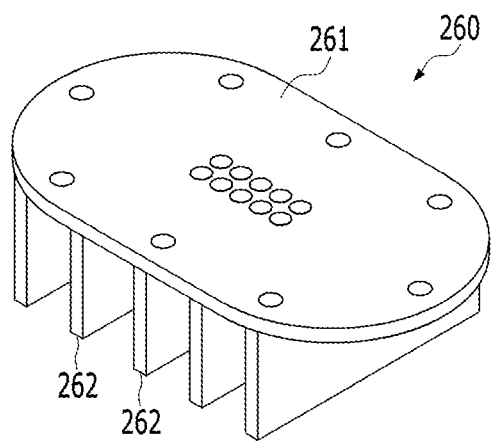
FIG. 10 is a view for explaining an example of a cooling unit according to the several exemplary embodiments of the present disclosure.

FIG. 10 is a view for explaining an example of the cooling unit according to the several exemplary embodiments of the present disclosure.

Referring to FIG. 10, the cooling unit 260 may include a heat radiating plate 261 and at least one heat radiating fin 262. However, the present disclosure is not limited thereto.

The heat radiating plate 261 may form a part of an upper surface of the cartridge 200. In this case, one surface of the heat radiating plate 261 may be provided inside the cartridge 200, and the other surface of the heat radiating plate 261 may be provided outside the cartridge 200. In this case, one surface of the heat radiating plate 261 may be in contact with the ultrasonic transmission medium, and the other surface of the heat radiating plate 261 may be in contact with air existing in the accommodation space 120 of the outer housing 100.

Meanwhile, the heat radiating plate 261 may be made of a material having high thermal conductivity so that the heat generated in the ultrasonic transmission medium may be efficiently dissipated to the outside.

For example, the heat radiating plate 261 may be made of a material such as silver, copper, gold, aluminum, alloy, carbon, or polymeric material. However, the present disclosure is not limited thereto.

Meanwhile, at least one heat radiating fin 262 may transfer the heat from the ultrasonic transmission medium to the heat radiating plate 261.

Specifically, at least one heat radiating fin 262 may be provided on one surface of the heat radiating plate 261 and may protrude toward the inside of the cartridge 200. In this case, an area where the cooling unit 260 is in contact with the ultrasonic transmission medium may be expanded by at least one heat radiating fin 262. Therefore, the heat generated in the ultrasonic transmission medium may be more quickly transferred to the cooling unit 260, and the heat generated in the ultrasonic transmission medium may be more quickly cooled down. However, the present disclosure is not limited thereto.

Meanwhile, according to the several exemplary embodiments of the present disclosure, at least one heat radiating fin 262 may be provided to have a matrix structure. However, the present disclosure is not limited thereto.

According to the above-mentioned configuration, the cartridge 200 may remove the heat generated in the ultrasonic transmission medium with the cooling unit 260. Therefore, it is possible to prevent at least one constituent element provided in the cartridge 200 from being damaged by the heat.

Meanwhile, according to the several exemplary embodiments of the present disclosure, a cooling fan for cooling the cooling unit 260 may be provided in the accommodation space 120 of the outer housing 100. Hereinafter, the cooling fan will be described with reference to FIG. 11.

Figure 11:
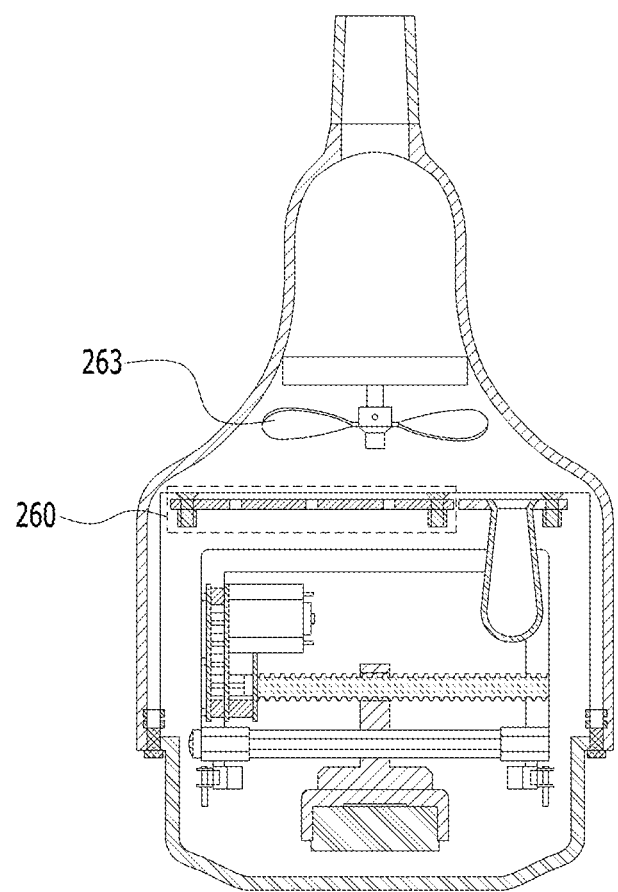
FIG. 11 is a cross-sectional view taken along line B-B' in FIG. 2 for explaining an example of a cooling fan according to the several exemplary embodiments of the present disclosure.

FIG. 11 is a cross-sectional view taken along line B-B' in FIG. 2 for explaining an example of the cooling fan according to the several exemplary embodiments of the present disclosure.

Referring to FIG. 11, a cooling fan 263 is provided in the outer housing 100 and may cool the cooling unit 260.

Specifically, the cooling fan 263 may be provided in the accommodation space 120 recessed to allow at least a part of the cartridge 200 to be inserted into the outer housing 100. Further, the cooling fan 263 may blow air toward the cooling unit 260 under control of the control unit 140. In this case, the heat generated in the ultrasonic transmission medium in the cartridge 200 may be more quickly removed. However, the present disclosure is not limited thereto.

Meanwhile, according to the several exemplary embodiments of the present disclosure, the cooling fan 263 may not be provided in the accommodation space 120.

Specifically, the outer housing 100 may be provided with a ventilation port penetratively formed to communicate with the accommodation space 120. In this case, the cooling fan 263 may be installed in the ventilation port.

Meanwhile, in the case in which the cooling fan 263 is installed in the ventilation port, the cooling fan 263 may rotate to discharge the air existing in the accommodation space 120 to the outside. Therefore, the air, which exists in the accommodation space 120 receiving the heat from the ultrasonic transmission medium, may be discharged to the outside by the cooling fan 263. However, the present disclosure is not limited thereto.

Meanwhile, according to the several exemplary embodiments of the present disclosure, the control unit 140 may control and rotate the cooling fan 263 in conjunction with the operation of the drive motor 241 of the drive unit 240.

According to several other exemplary embodiments of the present disclosure, the control unit 140 may control and rotate the cooling fan 263 in conjunction with the operation of controlling the ultrasonic transducer 230 to generate the ultrasound. However, the present disclosure is not limited thereto.

Meanwhile, according to the several exemplary embodiments of the present disclosure, the control unit 140 may control and operate the cooling fan 263 when a temperature in the cartridge 200, which is sensed by the sensing unit 224, is equal to or higher than a predetermined temperature. In this case, the sensing unit 224 may include a temperature sensor or the like.

Specifically, at least one temperature sensor may be provided in the cartridge 200. In this case, the control unit 140 may sense the temperature in the cartridge 200 by the sensing unit 224. Further, when the temperature in the cartridge 200 is equal to or higher than the predetermined temperature, the control unit 140 may control and operate the cooling fan 263. In this case, the predetermined temperature may be stored in advance in a storage unit. However, the present disclosure is not limited thereto.

According to the above-mentioned configuration, the heat generated in the ultrasonic transmission medium may be more quickly removed by the cooling fan 263.

Meanwhile, when the ultrasonic transmission medium is heated, a volume of the ultrasonic transmission medium may be expanded. In this case, a crack or fracture may be formed in the first casing 210 or the second casing 220 that forms an external appearance of the cartridge 200. Therefore, the buffer unit 270 may be provided in the cartridge 200 in order to prevent damage even though the volume of the ultrasonic transmission medium is expanded. Hereinafter, the buffer unit 270 will be described with reference to FIGS. 12 to 13.

Figure 12:
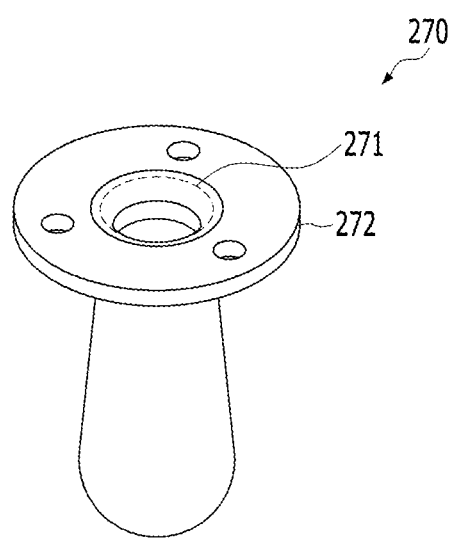
FIG. 12 is a view for explaining an example of a buffer unit according to the several exemplary embodiments of the present disclosure.

FIG. 12 is a view for explaining an example of the buffer unit according to the several exemplary embodiments of the present disclosure.

Referring to FIG. 12, the buffer unit 270 may have a tubular shape which is closed at one end thereof and has, at the other end thereof, an opening portion 271.

Specifically, a flange portion 272 is provided at the other end of the buffer unit 270, and at least a part of the buffer unit 270, except for the other end, may be disposed in the cartridge 200. In this case, the flange portion 272 may be coupled to an upper surface of the cartridge 200. Therefore, the opening portion 271 of the buffer unit 270 may be positioned outside the cartridge 200.

With the above-mentioned structure, the buffer unit 270 may be shrunk to maintain a constant pressure in the cartridge 200 when the ultrasonic transmission medium is expanded by heat, and the buffer unit 270 may be expanded to maintain the constant pressure in the cartridge 200 when the ultrasonic transmission medium is shrunk.

Specifically, the buffer unit 270 is shrunk when the ultrasonic transmission medium in the cartridge 200 is expanded by heat, such that the air in the buffer unit 270 may be discharged toward the outer housing 100 through the opening portion 271. In addition, when the ultrasonic transmission medium is cooled, the buffer unit 270 may be expanded in accordance with the volume of the shrunk ultrasonic transmission medium. However, the present disclosure is not limited thereto. Hereinafter, the configuration in which the ultrasonic transmission medium and the buffer unit 270 are shrunk or expanded will be further described with reference to FIG. 13.

Meanwhile, in the present disclosure, the buffer unit 270 may be made of rubber or the like. However, the present disclosure is not limited thereto.

Meanwhile, according to the several exemplary embodiments of the present disclosure, the buffer unit 270 may have a spacer (not illustrated) provided in an internal space formed by the opening portion 271.

Specifically, the buffer unit 270 may be shrunk when the ultrasonic transmission medium is expanded by heat. Further, an inner surface of the buffer unit 270 made of rubber or the like is formed by the opening portion 271, and portions of the inner surface of the buffer unit 270 may come into contact with each other as the buffer unit 270 is shrunk. If the portions of the inner surface of the buffer unit 270 are attached to each other and the buffer unit 270 cannot return to the original shape even though the heat in the ultrasonic transmission medium is removed and the volume of the ultrasonic transmission medium is shrunk, the pressure in the cartridge 200 may not be constantly maintained. Therefore, the buffer unit 270 may have the spacer that prevents the portions of the inner surface of the buffer unit 270 from being attached to one another when the buffer unit 270 is shrunk. In this case, the spacer may be formed to correspond to the internal shape of the buffer unit 270. However, the present disclosure is not limited thereto.

Meanwhile, in the present disclosure, the spacer may be made of polyurethane foam. However, the present disclosure is not limited thereto.

According to the above-mentioned configuration, the buffer unit 270 may prevent the cartridge 200 from being damaged even though the ultrasonic transmission medium, which fills the inside of the cartridge 200, is expanded by heat. In addition, the buffer unit 270 may maintain a constant pressure in the cartridge 200.

Hereinafter, the example in which the ultrasonic transmission medium and the buffer unit 270 are shrunk or expanded will be further described with reference to FIG. 13.

Figure 13:
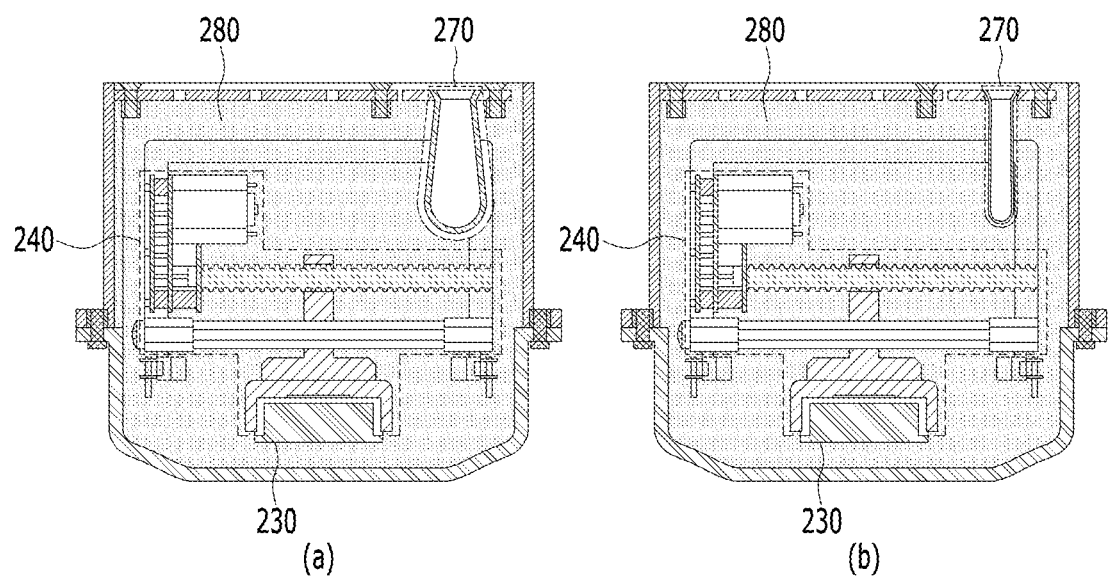
FIG. 13 is a view for explaining an example of an ultrasonic transmission medium and an example of a buffer unit according to the several exemplary embodiments of the present disclosure.

FIG. 13 is a view for explaining an example of the ultrasonic transmission medium and an example of the buffer unit according to the several exemplary embodiments of the present disclosure. FIG. 13A is a view for explaining a case in which the ultrasonic transmission medium according to the several exemplary embodiments of the present disclosure is expanded. FIG. 13B is a view for explaining a case in which the ultrasonic transmission medium according to the several exemplary embodiments of the present disclosure is shrunk.

Referring to FIG. 13A, the ultrasonic transmission medium 280 may receive the heat generated by at least one of the operations of the ultrasonic transducer 230 and the operation of the drive unit 240. In this case, the ultrasonic transmission medium 280 may be expanded. The cartridge 200 may be damaged as the ultrasonic transmission medium 280 is expanded.

Specifically, a crack or fracture may be formed in the first casing 210 or the second casing 220 that forms an external appearance of the cartridge 200. Therefore, the buffer unit 270 may be shrunk to the extent that the volume of the ultrasonic transmission medium 280 is expanded.

Meanwhile, referring to FIG. 13B, the pressure in the cartridge 200 may be decreased as the temperature of the ultrasonic transmission medium 280 is decreased. In this case, the buffer unit 270 may be expanded. However, the present disclosure is not limited thereto.

Meanwhile, according to the several exemplary embodiments of the present disclosure, the cartridge 200 may have a sealing member for preventing the ultrasonic transmission medium from leaking to the outside. Hereinafter, the sealing member will be described with reference to FIG. 14.

Figure 14:
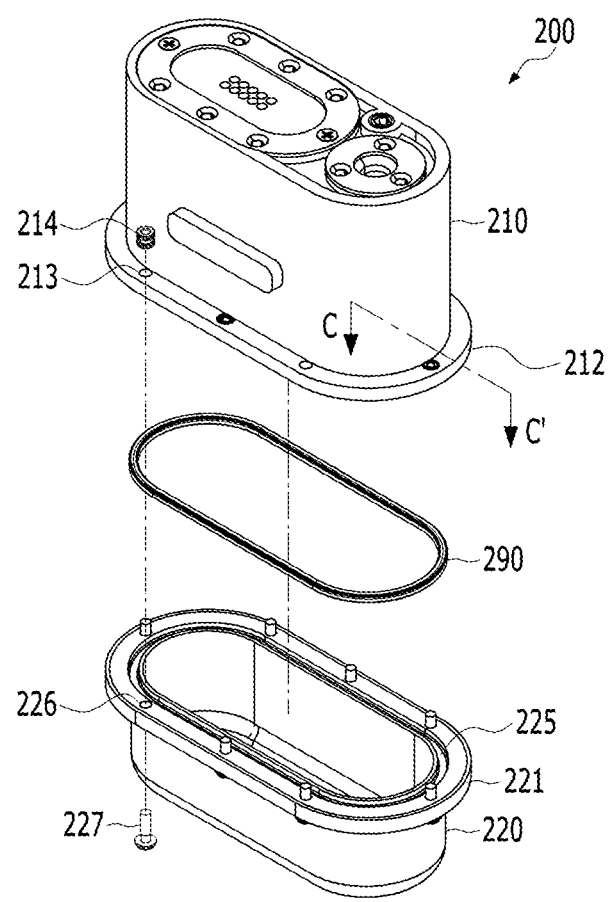
FIG. 14 is an exploded perspective view for explaining an example of a sealing member according to the several exemplary embodiments of the present disclosure.

FIG. 14 is an exploded perspective view for explaining an example of a sealing member according to the several exemplary embodiments of the present disclosure.

Referring to FIG. 14, the cartridge 200 may include the first casing 210, the second casing 220, and a sealing member 290. However, the present disclosure is not limited thereto.

The first casing 210 may include the first catching part 212, at least one first fastening hole 213, and at least one insert member 214. The second casing 220 may include the second catching part 221, a first sealing member groove 225, at least one second fastening hole 226, and at least one bolt 227. However, the present disclosure is not limited thereto.

At least one first fastening hole 213 is provided in the first catching part 212, and at least one bolt 227 may be fastened to the first fastening hole 213.

For example, at least one insert member 214 may be fixedly coupled in at least one first fastening hole 213. In this case, at least one insert member 214 may be a member having an internal thread so as to be fastened to at least one bolt 227. However, the present disclosure is not limited thereto.

Meanwhile, in the present disclosure, at least one insert member 214 may be made of a material more rigid than a material of the first casing 210.

For example, the first casing 210 may be made of a plastic-based or resin-based material. Further, at least one insert member 214 may be made of a material such as iron, copper, tin, stainless, an alloy, or the like. However, the present disclosure is not limited thereto.

Meanwhile, at least one second fastening hole 226 is provided in a region of the second catching part 221, and at least one bolt 227 may be fastened to the second fastening hole 226. In this case, the region may be a position corresponding to the position of at least one first fastening hole 213. That is, at least one second fastening hole may be provided at a position corresponding to at least one first fastening hole.

In this case, the first casing 210 and the second casing 220 may be coupled by at least one bolt 227 that penetrates at least one second fastening hole 226 and is fastened to at least one insert member 214. However, the present disclosure is not limited thereto.

Meanwhile, according to the several exemplary embodiments of the present disclosure, at least one insert member 214 may not be provided. In this case, at least one first fastening hole 213 may have the internal thread. Therefore, at least one bolt 227 may penetrate at least one second fastening hole 226 and may be fastened directly to at least one first fastening hole 213. However, the present disclosure is not limited thereto.

Meanwhile, according to the several exemplary embodiments of the present disclosure, a screw thread may be formed only in one region of at least one bolt 227. In this case, the region may be a region corresponding to the position at which at least one bolt 227 is fastened to at least one first fastening hole 213. However, the present disclosure is not limited thereto.

Meanwhile, the first sealing member groove 225 may be provided in an upper surface of the second catching part 221.

Specifically, the cartridge 200 may have the sealing member 290 provided between the first casing 210 and the second casing 220 to prevent the ultrasonic transmission medium 280 from leaking to the outside. In this case, the sealing member 290 may be seated in the first sealing member groove 225 provided in the upper surface of the second catching part 221. However, the present disclosure is not limited thereto.

Meanwhile, according to the several exemplary embodiments of the present disclosure, a shape of the first sealing member groove 225 may correspond to a shape of the sealing member 290. In this case, the sealing member 290 may be seated in the first sealing member groove 225. However, the present disclosure is not limited thereto.

Meanwhile, according to the several exemplary embodiments of the present disclosure, the shape of the first sealing member groove 225 may not correspond to the shape of the sealing member 290.

Specifically, the sealing member 290 according to the present disclosure may be made of a rubber-based or resin-based material. In this case, the external shape of the sealing member 290 made of a rubber-based or resin-based material may be deformed to some extent by elastic force. For example, the original shape of the sealing member 290 is maintained when no external force is applied, but when the external force is applied, the sealing member 290 may be deformed to have a shape that may be inserted into the first sealing member groove 225. Therefore, the shape of the first sealing member groove 225 may not correspond to the shape of the sealing member 290. However, the present disclosure is not limited thereto.

Meanwhile, according to the several exemplary embodiments of the present disclosure, a height of the first sealing member groove 225 may be equal to or smaller than a height of the sealing member 290. In this case, when the sealing member 290 is seated in the first sealing member groove 225, at least a part of an external appearance of the sealing member 290 may protrude outward from the first sealing member groove 225. Meanwhile, in the case in which at least a part of the sealing member 290 protrudes outward from the first sealing member groove 225, the sealing member 290 may be compressed as the first casing 210 and the second casing 220 are coupled to each other.

Specifically, when the first casing 210 and the second casing 220 are fastened by at least one bolt 227, the lower surface of the first catching part 212 and the upper surface of the second catching part 221 may be coupled to be in contact with each other. In this case, the sealing member 290, which at least partially protrudes outward from the first sealing member groove 225, may be compressed. Therefore, it is possible to prevent a leak of the ultrasonic transmission medium 280 received in the cartridge 200. However, the present disclosure is not limited thereto.

Meanwhile, according to the several exemplary embodiments of the present disclosure, the plurality of sealing members 290 and the plurality of first sealing member grooves 225 may be provided.

For example, the cartridge 200 may have at least two sealing members having different outer diameters. Further, at least two first sealing member grooves, which correspond to outer diameters of at least two sealing members, respectively, may be formed at the upper end of the second catching part 221. However, the present disclosure is not limited thereto.

Meanwhile, according to several other exemplary embodiments of the present disclosure, a second sealing member groove, into which the sealing member 290 is inserted, may be provided in the lower surface of the first catching part 212. However, the present disclosure is not limited thereto.

Meanwhile, according to several other exemplary embodiments of the present disclosure, a shape of the second sealing member groove may correspond to the shape of the sealing member 290. In this case, the sealing member 290 may be inserted into the second sealing member groove. However, the present disclosure is not limited thereto.

Meanwhile, according to several other exemplary embodiments of the present disclosure, the shape of the second sealing member groove may not correspond to the shape of the sealing member 290. However, the present disclosure is not limited thereto.

Meanwhile, according to several other exemplary embodiments of the present disclosure, a height of the second sealing member groove may be equal to or smaller than a height of the sealing member 290. In this case, when the sealing member 290 is seated in the second sealing member groove, at least a part of an external appearance of the sealing member 290 may protrude outward from the second sealing member groove.

Meanwhile, in the case in which at least a part of the sealing member 290 protrudes outward from the second sealing member groove, the sealing member 290 may be compressed as the first casing 210 and the second casing 220 are coupled to each other. However, the present disclosure is not limited thereto.

Meanwhile, according to the several exemplary embodiments of the present disclosure, both the first catching part 212 and the second catching part 221 may have the sealing member grooves, respectively.

Specifically, the first catching part 212 may have a third sealing member groove provided in the lower surface of the first catching part 212, and the second catching part 221 may have a fourth sealing member groove provided in the upper surface of the second catching part 221. In this case, a position of the first catching part 212 where the third sealing member groove is provided may correspond to a position of the second catching part 221 where the fourth sealing member groove is provided.

Meanwhile, in the case in which the position at which the third sealing member groove is provided and the position at which the fourth sealing member groove is provided correspond to each other, a height of the third sealing member groove and a height of the fourth sealing member groove may be equal to or smaller than a height of the sealing member 290.

Specifically, when the first casing 210 and the second casing 220 are coupled, a height dimension may be made by adding up the height of the third sealing member groove and the height of the fourth sealing member groove. In this case, the made height dimension may be equal to or smaller than the height of the sealing member 290.

Meanwhile, the sealing member 290 may be compressed as the first casing 210 and the second casing 220 are coupled to each other. However, the present disclosure is not limited thereto.

Meanwhile, according to several other exemplary embodiments of the present disclosure, the position of the first catching part 212 where the third sealing member groove is provided may be different from the position of the second catching part 221 where the fourth sealing member groove is provided. That is, a diameter of the third sealing member groove and a diameter of the fourth sealing member groove may be different from each other. In this case, the plurality of sealing members 290 may be provided to be inserted into the third sealing member groove and the fourth sealing member groove, respectively. However, the present disclosure is not limited thereto.

Meanwhile, according to several other exemplary embodiments of the present disclosure, the casings may include at least one additional casing in addition to the first casing 210 and the second casing 220. In this case, the above-mentioned sealing structure may be provided at a portion where one casing and another casing are coupled to each other. However, the present disclosure is not limited thereto.

According to the above-mentioned configuration, the sealing member 290 may be provided to be compressed between the first casing 210 and the second casing 220. Therefore, it is possible to prevent a leak of the ultrasonic transmission medium 280 that fills the internal filling space formed by coupling the first casing 210 and the second casing 220.

Meanwhile, in the present disclosure, at least one insert member 214 may be inserted into at least one first fastening hole 213. Hereinafter, at least one insert member 214 fixedly coupled to the inside of at least one first fastening hole 213 will be further described with reference to FIG. 15.

Figure 15:
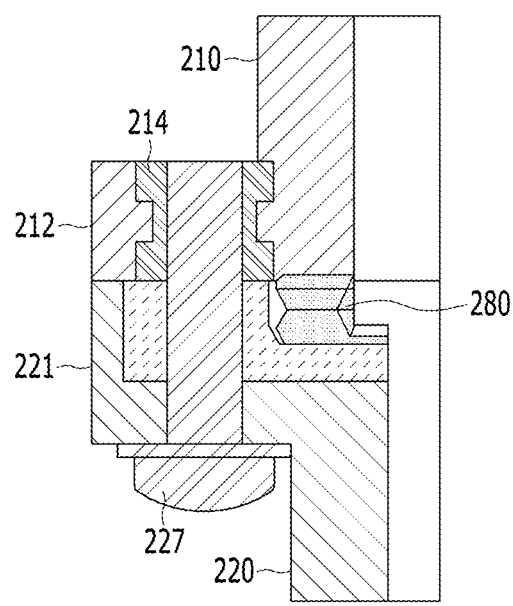
FIG. 15 is a cross-sectional view taken along line C-C' in FIG. 14 for explaining an example of a method of fastening a first casing and a second casing according to the several exemplary embodiments of the present disclosure.

FIG. 15 is a cross-sectional view taken along line C-C' in FIG. 14 for explaining an example of a method of fastening the first casing and the second casing according to the several exemplary embodiments of the present disclosure.

Referring to FIG. 15, at least one bolt 227 may couple the first casing 210 and the second casing 220.

Specifically, regarding at least one bolt 227, at least one insert member 214 may be inserted into at least one first fastening hole 231 provided in the first catching part 212. In this case, at least one bolt 227 may be fastened to at least one insert member 214 and may penetrate at least one second fastening hole 226 provided in the second catching part 221 without being fastened to at least one second fastening hole 226.

Meanwhile, an outer diameter of at least one insert member 214 may correspond or be equal to an inner diameter of at least one first fastening hole 231. In this case, at least one insert member 214 may be fitted with or coupled, by an interference fit, to at least one first fastening hole 231. In this case, the fit or the interference fit may refer to a relationship in which two components are joined to each other with a gap and a clearance made by a dimensional difference before the two components are fitted with each other. Further, a tolerance for this purpose may depend on standards such as ISO, ASTM, and DIN. However, the present disclosure is not limited thereto.

According to the above-mentioned configuration, at least one insert member 214 may be inserted and coupled to at least one first fastening hole 213. In this case, a screw thread may be formed directly on at least one first fastening hole 213, such that it is possible to reduce cracks or damage that may occur when at least one bolt 227 is fastened.

Meanwhile, in the present disclosure, the sensing unit 224, which recognizes contact with at least a part of the user's body, may be provided in a partial region of the lower part of the cartridge 200. In this case, the control unit 140 may recognize the contact between at least a part of the user's body and the cartridge 200 by the sensing unit 224.

Hereinafter, the sensing unit 224 according to the present disclosure will be described with reference to FIGS. 16 and 17.

Figure 16:
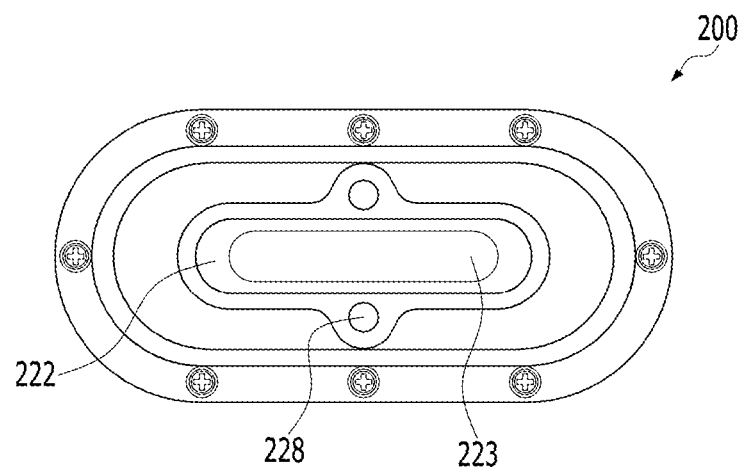
FIG. 16 is a bottom view for explaining an example of a sensing unit according to the several exemplary embodiments of the present disclosure.

FIG. 16 is a bottom view for explaining an example of the sensing unit according to the several exemplary embodiments of the present disclosure.

Referring to FIG. 16, the cartridge 200 may include the action part 222 and at least two electrode parts 228. However, the present disclosure is not limited thereto.

The action part 222 is at least partially positioned on the extension line of the vertical cross-section of the outer housing 100 and may be a region in which the high intensity focused ultrasound created from the high intensity focused ultrasound device 10 is transmitted to the outside. Therefore, the action part 222 may include at least two electrode parts 228 and the window 223. However, the present disclosure is not limited thereto.

Meanwhile, in the present disclosure, each of at least two electrode parts 228 may be provided in a region protruding from the action part 222 in a lateral direction. That is, the action part 222 may have a cross shape when viewing the high intensity focused ultrasonic device 10 from the bottom side. Further, at least two electrode parts 228 may be provided to come into contact with at least a part of the user's body.

Meanwhile, at least two electrode parts 228 may apply an electric current.

Specifically, at least two electrode parts 228 may apply the electric current having a predetermined frequency to at least a part of the body. In this case, the frequency may be a multi-frequency signal having frequencies within a range from 1 kHz to 10 MHz. However, the present disclosure is not limited thereto.

For example, as illustrated in FIG. 16, at least two electrode parts 228 may include an upper electrode part positioned at an upper side of the action part 222, and a lower electrode part positioned at a lower side of the action part 222. In this case, the control unit 140 may apply, to the upper electrode part, the electric current having a predetermined frequency. In this case, the electric current may return to the lower electrode part after passing through the user's body. However, the present disclosure is not limited thereto.

Meanwhile, a measurement unit (not illustrated) may apply a voltage to at least two electrode parts 228 and may measure the electric current corresponding to the applied voltage.

For example, the measurement unit may measure a difference in voltage between the upper electrode part and the lower electrode part. However, the present disclosure is not limited thereto.

Meanwhile, a contact recognizing unit (not illustrated) may create an impedance value based on the voltage applied by the measurement unit and the electric current measured by the measurement unit, and the contact recognizing unit may recognize the contact based on the impedance value.

For example, data in respect to a range of impedance values related to human skin may be stored in advance in the storage unit. In this case, when the contact recognizing unit recognizes that the created impedance value is within the range stored in advance, the contact recognizing unit may recognize that at least two electrode parts 228 are in contact with at least a part of the body. However, the present disclosure is not limited thereto.

Meanwhile, according to the several exemplary embodiments of the present disclosure, when the sensing unit 224 recognizes that the action part 222 or at least two electrode parts 228 are in contact with at least a part of the body, the control unit 140 may control the ultrasonic transducer 230 to generate the ultrasound.

Meanwhile, according to the several exemplary embodiments of the present disclosure, when the sensing unit 224 recognizes that at least two electrode parts 228 are in contact with at least a part of the body and a touch input through the user input unit 111 is recognized, the control unit 140 may control the high intensity focused ultrasound device to generate the high intensity focused ultrasound. Hereinafter, a method of controlling, by the control unit 140, the ultrasonic transducer 230 by means of the sensing unit 224 will be described below with reference to FIGS. 19 and 21.

Meanwhile, according to the several exemplary embodiments of the present disclosure, the control unit 140 may recognize the contact with at least a part of the user's body by using a sensor pattern. Hereinafter, another example of the sensing unit 224 according to the present disclosure will be described with reference to FIG. 17.

Figure 17:
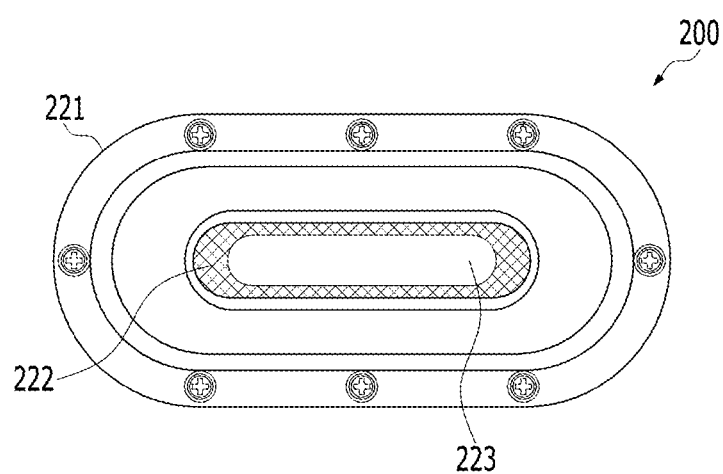
FIG. 17 is a bottom view for explaining an example of a sensing unit according to several other exemplary embodiments of the present disclosure.

FIG. 17 is a bottom view for explaining an example of a sensing unit according to several other exemplary embodiments of the present disclosure.

Referring to FIG. 17, a sensor pattern part 229 may be provided on the lower surface of the cartridge 200 so as to come into contact with at least a part of the user's body.

In this case, the sensor pattern part 229 serves to detect the presence or absence of the touch input when at least a part of the body approaches the sensor pattern part 229, and the sensor pattern part 229 may be made of a transparent conductor or metal.

For example, the sensor pattern part 229 is made of a transparent conductor such as indium tin oxide (ITO), antimony tin oxide (ATO), carbon nano tube (CNT), and indium zinc oxide (IZO). However, the present disclosure is not limited thereto.

Meanwhile, in the present disclosure, the sensor pattern part 229 may be in the form of a dot matrix arranged in a matrix shape, and the sensor pattern part 229 may be arranged such that linear patterns may be arranged in longitudinal and transverse directions. However, the present disclosure is not limited thereto.

A touch detecting unit (not illustrated) is connected to the sensor pattern part and may detect a touch signal by detecting a voltage variation value of the sensor pattern part when touch capacitance is added.

Specifically, the touch detecting unit may detect whether a signal level varies in the sensor pattern part.

For example, the touch detecting unit may obtain the touch signal by detecting a difference in magnitude between a voltage when no touch occurs on the sensor pattern part and a voltage when the touch occurs. However, the present disclosure is not limited thereto.

Meanwhile, the contact recognizing unit (not illustrated) may recognize the contact based on the touch signal detected by the touch detecting unit.

For example, when the touch detecting unit obtains the touch signal, the contact recognizing unit may recognize that the sensor pattern part 229 is in contact with at least a part of the user's body. However, the present disclosure is not limited thereto.

Meanwhile, according to the several exemplary embodiments of the present disclosure, when the sensing unit 224 recognizes that the sensor pattern part 229 is in contact with at least a part of the body, the control unit 140 may control the ultrasonic transducer 230 to generate the ultrasound.

Meanwhile, according to the several exemplary embodiments of the present disclosure, when the sensing unit 224 recognizes that the sensor pattern part 229 is in contact with at least a part of the body and a touch input is recognized through the user input unit 111, the control unit 140 may control the high intensity focused ultrasound device to generate the high intensity focused ultrasound. Hereinafter, a method of controlling, by the control unit 140, the ultrasonic transducer 230 by means of the sensing unit 224 will be described below with reference to FIGS. 19 to 21.

Meanwhile, according to the several exemplary embodiments of the present disclosure, the control unit 140 may control the ultrasonic transducer 230 to generate the ultrasound in a first mode or a second mode based on the user's input inputted through the user input unit 111. Hereinafter, an example of the method of controlling the ultrasonic transducer 230 by the control unit 140 will be described with reference to FIG. 18.

Figure 18:
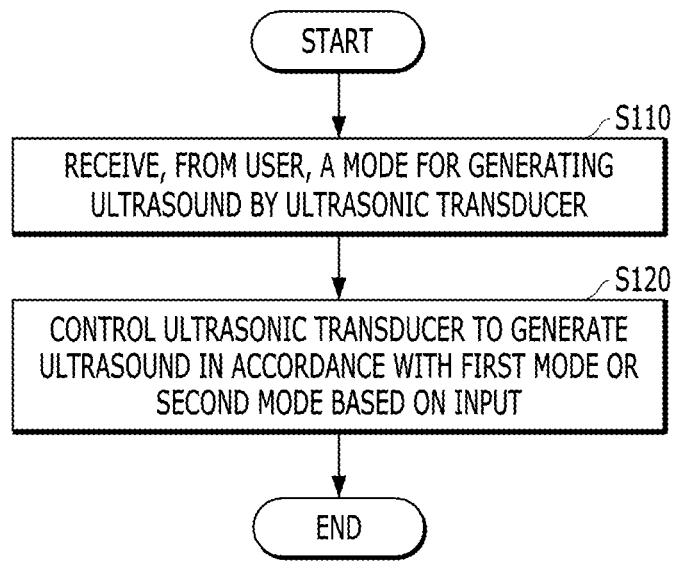
FIG. 18 is a flowchart for explaining an example of a method of operating, by a control unit, an ultrasonic transducer according to the several exemplary embodiments of the present disclosure.

FIG. 18 is a flowchart for explaining an example of a method of operating, by the control unit, the ultrasonic transducer according to the several exemplary embodiments of the present disclosure.

Referring to FIG. 18, the control unit 140 may receive, from the user through the user input unit 111, a mode for generating the ultrasound by the ultrasonic transducer 230 (S110). In this case, the mode is a method of generating the ultrasound by the ultrasonic transducer 230, and the mode may be stored in advance in the storage unit. However, the present disclosure is not limited thereto.

Meanwhile, according to the several exemplary embodiments of the present disclosure, the user input unit 111 may receive the touch input from the user through the touch sensor. However, the present disclosure is not limited thereto.

Meanwhile, in the present disclosure, the mode inputted by the user through the user input unit 111 may be displayed on a display unit (not illustrated) provided on the high intensity focused ultrasound device 10 or a display unit provided on an external device (not illustrated) connected to a light output part (not illustrated) or the high intensity focused ultrasound device 10. However, the present disclosure is not limited thereto.

Meanwhile, the control unit 140 may control the ultrasonic transducer 230 to generate the ultrasound in accordance with the first mode or the second mode based on the input from the user (S120).

In this case, the input from the user may be the touch input made by the touch sensor or an input made by a mechanical input means. However, the present disclosure is not limited thereto.

Meanwhile, the first mode may be a mode that discontinuously generates the ultrasound at a predetermined time interval. In this case, the predetermined time interval may be stored in advance in the storage unit. However, the present disclosure is not limited thereto.

For example, the control unit 140 may control the ultrasonic transducer 230 to have a cycle in which the ultrasound is generated for one second and no ultrasound is generated for one second. However, the present disclosure is not limited thereto.

Meanwhile, the second mode may be a mode that continuously generates the ultrasound for a predetermined period of time.

For example, when the predetermined time stored in advance in the storage unit is one minute and it is recognized that the second mode is inputted, the control unit 140 may control the ultrasonic transducer 230 to generate the ultrasound for one minute. However, the present disclosure is not limited thereto.

Meanwhile, according to the several exemplary embodiments of the present disclosure, the control unit 140 may control the ultrasonic transducer 230 to generate the ultrasound in accordance with a fourth mode. In this case, the fourth mode may be a mode that continuously generates the ultrasound while the touch input is recognized. However, the present disclosure is not limited thereto.

Meanwhile, according to the several exemplary embodiments of the present disclosure, the control unit 140 may control the ultrasonic transducer 230 to continuously generate the ultrasound based on the input from the user until a next input is generated. That is, the user may turn on/off the ultrasonic transducer 230 through the user input unit 111. However, the present disclosure is not limited thereto.

According to the above-mentioned configuration, the control unit 140 may control the ultrasonic transducer 230 to generate the ultrasound based on the input from the user.

Meanwhile, when the sensing unit 224 recognizes the contact with at least a part of the user's body, the control unit 140 may control the ultrasonic transducer 230 to generate the ultrasound. Hereinafter, an example of the method of controlling the ultrasonic transducer 230 by the control unit 140 will be described with reference to FIG. 19.

Figure 19:
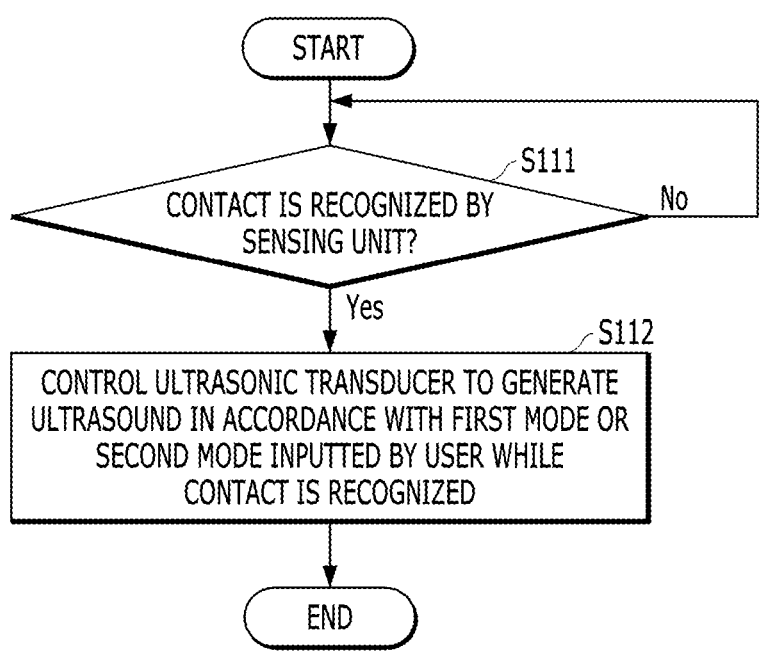
FIG. 19 is a flowchart for explaining an example of a method of operating, by the control unit, the ultrasonic transducer according to the several exemplary embodiments of the present disclosure when a user's body is partially in contact with an action part.

FIG. 19 is a flowchart for explaining an example of a method of operating, by the control unit, the ultrasonic transducer according to the several exemplary embodiments of the present disclosure when the user's body is partially in contact with the action part.

Referring to FIG. 19, the control unit 140 may recognize, through the sensing unit 224, that the action part 222 is in contact with a part of the user's body (S111, Yes). Further, the control unit 140 may control the ultrasonic transducer 230 to generate the ultrasound in accordance with the first mode or the second mode inputted by the user while the contact is recognized (S112).

For example, the control unit 140 may recognize that the action part 222 is in contact with at least a part of the user's body, through at least two electrode parts 228 according to the several exemplary embodiments of the present disclosure. As another example, the control unit 140 may recognize that the action part 222 is in contact with at least a part of the user's body through the sensor pattern part 229 according to several other exemplary embodiments of the present disclosure.

In this case, the control unit 140 may control the ultrasonic transducer 230 to generate the ultrasound in accordance with the first mode or the second mode. However, the present disclosure is not limited thereto.

Meanwhile, when the sensing unit 224 recognizes that the action part 222 is not in contact with a part of the user's body (S111, No), the control unit 140 may control the ultrasonic transducer 230 so as not to generate the ultrasound. Further, the control unit 140 may periodically or non-periodically ascertain, through the sensing unit 224, whether the action part 222 is in contact with a part of the user's body. However, the present disclosure is not limited thereto.

Meanwhile, according to the present disclosure, if the predetermined period of time has passed, the control unit 140 may control the ultrasonic transducer 230 so as not to generate the ultrasound even while the sensing unit 224 recognizes the contact with a part of the user's body.

For example, the control unit 140 may receive, from the user through the user input unit 111, the second mode that continuously generates the ultrasound for a predetermined period of time. In this case, the predetermined time may be 2 minutes. If two minutes passed while the sensing unit 224 recognizes the contact, the control unit 140 may control the ultrasonic transducer 230 so as not to generate the ultrasound even though the contact is being recognized. In this case, it is possible to prevent a safety accident that may occur when the high intensity focused ultrasound device 10 inadvertently emits the ultrasound over a long period of time. However, the present disclosure is not limited thereto.

Meanwhile, according to the several exemplary embodiments of the present disclosure, when the sensing unit 224 recognizes the contact and the touch input is recognized through the user input unit 111, the control unit 140 may control the ultrasonic transducer 230 to generate the high intensity focused ultrasound. However, the present disclosure is not limited thereto.

According to the above-mentioned exemplary embodiment, the user may more conveniently use the high intensity focused ultrasound device 10.

Meanwhile, in the present disclosure, the control unit 140 may control the ultrasonic transducer 230 to generate the ultrasound while the contact is recognized by the sensing unit 224. Another method of controlling the ultrasonic transducer 230 by the control unit 140 will be described with reference to FIG. 20.

Figure 20:
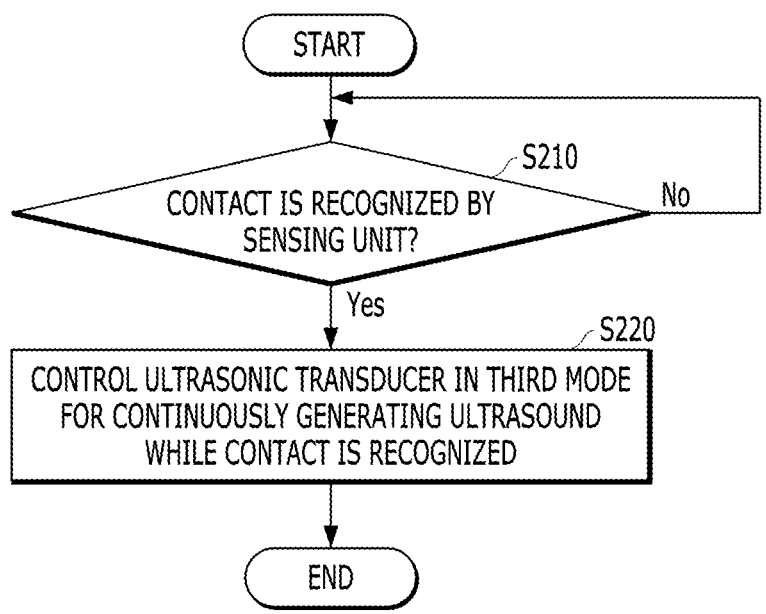
FIG. 20 is a flowchart for explaining of an example of a method of operating, by the control unit, the ultrasonic transducer according to several other exemplary embodiments of the present disclosure when the user's body is partially in contact with the action part.

FIG. 20 is a flowchart for explaining of an example of a method of operating, by the control unit, the ultrasonic transducer according to several other exemplary embodiments of the present disclosure when the user's body is partially in contact with the action part.

According to the several exemplary embodiments of the present disclosure, a third mode may further be stored in the storage unit in addition to the first mode and the second mode described with reference to FIGS. 18 and 19. In this case, the third mode may be a mode that continuously generates the ultrasound while the action part 222 is in contact with at least a part of the user's body.

The control unit 140 may receive, through the user input unit 111, an input for generating the ultrasound in accordance with the third mode. In this case, the control unit 140 may control the ultrasonic transducer 230 to generate the ultrasound in accordance with the third mode.

Specifically, referring to FIG. 20, the control unit 140 may recognize, through the sensing unit 224, that the action part 222 is in contact with a part of the user's body (S210, Yes). Further, the control unit 140 may control the ultrasonic transducer 230 in accordance with the third mode that continuously generates the ultrasound while the contact is recognized (S220).

That is, the control unit 140 may control the ultrasonic transducer 230 to consistently generate the ultrasound while the sensing unit 224 recognizes the contact.

In this case, the user may conveniently and continuously perform a procedure on a diseased part of a patient without considering the elapse of the predetermined time. However, the present disclosure is not limited thereto.

Meanwhile, when the sensing unit 224 recognizes that the action part 222 is not in contact with a part of the user's body (S210, No), the control unit 140 may control the ultrasonic transducer 230 so as not to generate the ultrasound. Further, the control unit 140 may periodically or non-periodically ascertain, through the sensing unit 224, whether the action part 222 is in contact with a part of the user's body. However, the present disclosure is not limited thereto.

According to the above-mentioned configuration, the user may conveniently generate the ultrasound only by bringing the action part 222 of the high intensity focused ultrasound device 10 into contact with a part of the user's body.

Meanwhile, in the present disclosure, the control unit 140 may control the ultrasonic transducer 230 to generate the ultrasound based on the movement of the moving module 245. Hereinafter, a method of controlling, by the control unit 140, the ultrasonic transducer 230 by the drive unit 240 will be described with reference to FIG. 21.

Figure 21:
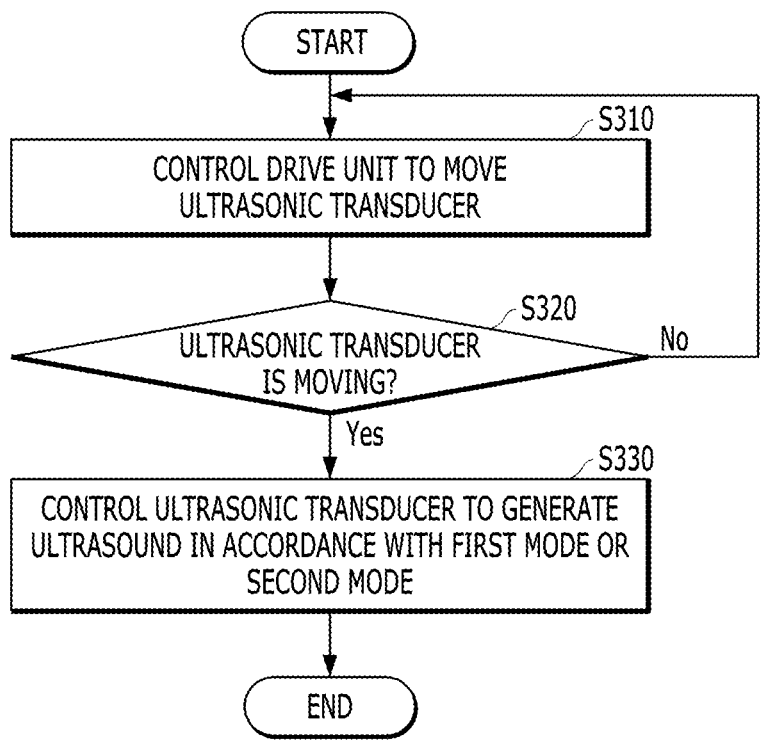
FIG. 21 is a flowchart for explaining an example of a method of operating, by the control unit, the ultrasonic transducer by means of the drive unit according to the several exemplary embodiments of the present disclosure.

FIG. 21 is a flowchart for explaining an example of a method of operating, by the control unit, the ultrasonic transducer by means of the drive unit according to the several exemplary embodiments of the present disclosure.

Referring to FIG. 21, the control unit 140 may control the drive unit 240 to move the moving module 245 that secures the ultrasonic transducer 230 (S310).

For example, the control unit 140 may control the moving module 245 to horizontally move the ultrasonic transducer 230 in the cartridge 200. However, the present disclosure is not limited thereto.

Meanwhile, when it is recognized that the ultrasonic transducer 230 is moving (S320, Yes), the control unit 140 may control the ultrasonic transducer 230 to generate the ultrasound in accordance with the first mode or the second mode (S330).

As an example, in a case in which the first mode is inputted from the user, the control unit 140 may discontinuously generate the ultrasound at a predetermined time interval while the ultrasonic transducer 230 moves horizontally in the cartridge 200.

As another example, in a case in which the second mode is inputted from the user, the control unit 140 may continuously generate the ultrasound for a predetermined period of time while the ultrasonic transducer 230 moves horizontally in the cartridge 200. However, the present disclosure is not limited thereto.

Meanwhile, when it is not recognized that the ultrasonic transducer 230 is moving (S320, No), the control unit 140 may control the ultrasonic transducer 230 so as not to generate the ultrasound (S330). Further, the control unit 140 may control the drive unit 240 to move the ultrasonic transducer 230 (S310).

As illustrated in FIGS. 1 to 21, the high intensity focused ultrasound device 10 according to the present disclosure may have the action part 222 on the extension line of the vertical cross-section of the gripping part 110. Therefore, the user may easily grip the gripping part 110 of the outer housing 100 and bring the cartridge 200 into contact with the skin.

The description of the presented exemplary embodiments is provided to enable any person skilled in the art of the present disclosure to carry out or use the present disclosure. Various modifications to the exemplary embodiments will be apparent to those skilled in the art of the present disclosure, and the generic principles defined herein may be applied to other exemplary embodiments without departing from the scope of the present disclosure. Accordingly, it should be understood that the present disclosure is not limited to the exemplary embodiments presented herein but should be construed in the broadest scope consistent with the principles and novel features presented herein.

What is claimed is:

1. A high intensity focused ultrasound device delivering high intensity focused ultrasound comprising:
   an outer housing comprising at least one coupling hole;
   a grip comprising a part of the outer housing grippable by a user; and
   a cartridge positioned at least partially on an extension line of a vertical cross-section of the grip, wherein the cartridge allows high intensity focused ultrasound generated from the high intensity focused ultrasound device to be transmitted to an outside;
   a coupling structure disposed on the cartridge and comprising at least one coupling part, wherein the at least one coupling part couples with the outer housing via the at least one coupling hole, such that the cartridge is detachably coupled with the outer housing in a vertical direction;
   a drive unit positioned in the cartridge and coupled to an ultrasonic transducer that generates an ultrasound, wherein the drive unit comprises a drive motor;
   an ultrasonic transmission medium disposed within an interior of the cartridge, wherein the ultrasonic transmission medium transmits to the outside the ultrasound generated by the ultrasonic transducer;
   wherein the ultrasonic transmission medium is oil;
   a cooling unit disposed within the cartridge that removes heat of the ultrasonic transmission medium;
   a cooling fan disposed in the outer housing and configured to cool the cooling unit of the cartridge; and a buffer unit at least partially disposed within the cartridge, wherein the buffer unit is configured to expand and shrink to maintain a constant pressure within the cartridge, wherein the buffer unit is closed at a first end disposed within the cartridge and has an opening at a second end opposite the first end.

2. The high intensity focused ultrasound device of claim 1, wherein the cartridge is detachably coupled to a lower side of the outer housing in the vertical direction.

3. The high intensity focused ultrasound device of claim 1, further comprising:
   an action part provided in a lower part of the cartridge.

4. The high intensity focused ultrasound device of claim 1, wherein a vertical center axis of the outer housing is located in a straight line with a vertical center axis of the cartridge.

5. The high intensity focused ultrasound device of claim 1, wherein the coupling structure comprises a hook coupling structure, a fitting coupling structure, or a screw coupling structure.

6. The high intensity focused ultrasound device of claim 5, wherein the hook coupling structure is formed by at least one hook extending from the outer housing toward the cartridge and at least one hook groove provided in the cartridge to which the at least one hook is coupled.

7. The high intensity focused ultrasound device of claim 5, wherein the hook coupling structure is formed by at least one hook protruding from a region of the cartridge and at least one hook groove provided in the outer housing to which the at least one hook is coupled.

8. The high intensity focused ultrasound device of claim 5, wherein the fitting coupling structure is formed by an accommodation space recessed in the outer housing and a region of the cartridge inserted into the accommodation space.

9. The high intensity focused ultrasound device of claim 8, wherein a shape of the accommodation space corresponds to a shape of the region of the cartridge.

10. The high intensity focused ultrasound device of claim 5, wherein the screw coupling structure is formed by a rotational engagement of a screw thread existing in an accommodation space recessed in the outer housing and a screw thread existing in a region of the cartridge inserted into the accommodation space.

11. The high intensity focused ultrasound device of claim 1, wherein the outer housing comprises the at least one coupling hole formed through penetration to communicate with an accommodation space recessed in the outer housing, and wherein the cartridge, in case at least partially inserted in the accommodation space, comprises the at least one coupling part which is formed to protrude outwards of the at least one coupling hole when being inserted into the at least one coupling hole.

12. The high intensity focused ultrasound device of claim 11, wherein a shape of the at least one coupling part corresponds to a shape of the at least one coupling hole.

13. The high intensity focused ultrasound device of claim 1, wherein the buffer unit comprises a tubular shape.

14. The high intensity focused ultrasound device of claim 13, wherein the opening at the second end of the buffer unit is positioned outside of the cartridge.

15. The high intensity focused ultrasound device of claim 14, wherein air within the buffer unit is discharged toward the outer housing when the buffer unit is shrunk.

16. The high intensity focused ultrasound device of claim 1, wherein the cooling unit comprises a heat radiating plate and at least one heat radiating fin, optionally, wherein the heat radiating plate forms a part of an upper surface of the cartridge.

17. The high intensity focused ultrasound device of claim 1, wherein the outer housing further comprises a ventilation port, and wherein the cooling fan is installed in the ventilation port.

* * * * *